US009522195B2

(12) United States Patent
Grasso et al.

(10) Patent No.: US 9,522,195 B2
(45) Date of Patent: *Dec. 20, 2016

(54) ANTIBODIES WITH IMMUNE EFFECTOR ACTIVITY AND THAT INTERNALIZE IN FOLATE RECEPTOR ALPHA-POSITIVE CELLS

(71) Applicant: Morphotek, Inc., Exton, PA (US)

(72) Inventors: Luigi Grasso, Bryn Mawr, PA (US); Nicholas C. Nicolaides, Garnett Valley, PA (US); Philip M. Sass, Audubon, PA (US)

(73) Assignee: Morphotek, Inc., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/809,887

(22) Filed: Jul. 27, 2015

(65) Prior Publication Data

US 2016/0058885 A1 Mar. 3, 2016

Related U.S. Application Data

(60) Continuation of application No. 13/356,724, filed on Jan. 24, 2012, now Pat. No. 9,144,614, which is a continuation of application No. 12/503,983, filed on Jul. 16, 2009, now Pat. No. 8,124,083, which is a division of application No. 11/410,442, filed on Apr. 24, 2006, now abandoned.

(60) Provisional application No. 60/674,185, filed on Apr. 22, 2005.

(51) Int. Cl.
| | | |
|---|---|---|
| *C07K 16/28* | (2006.01) | |
| *C07K 16/30* | (2006.01) | |
| *A61K 47/48* | (2006.01) | |
| *B82Y 5/00* | (2011.01) | |
| *A61K 31/704* | (2006.01) | |

(52) U.S. Cl.
CPC ....... *A61K 47/48638* (2013.01); *A61K 31/704* (2013.01); *A61K 47/48469* (2013.01); *A61K 47/48569* (2013.01); *A61K 47/48746* (2013.01); *B82Y 5/00* (2013.01); *C07K 16/28* (2013.01); *C07K 16/30* (2013.01); *C07K 16/3069* (2013.01); *C07K 2317/24* (2013.01); *C07K 2317/732* (2013.01); *C07K 2317/77* (2013.01)

(58) Field of Classification Search
CPC .................. A61K 47/48469; A61K 47/48746; C07K 16/28; C07K 16/30; C07K 16/3069; C07K 2317/24; C07K 2317/732; C07K 2317/77
USPC ........................................... 424/133.1, 174.1
See application file for complete search history.

(56) References Cited

U.S. PATENT DOCUMENTS

| | | |
|---|---|---|
| 4,694,778 A | 9/1987 | Learn et al. |
| 4,851,332 A | 7/1989 | Rettig et al. |
| 5,006,470 A | 4/1991 | Yamaguchi et al. |
| 5,108,921 A | 4/1992 | Low et al. |
| 5,320,956 A | 6/1994 | Willingham et al. |
| 5,416,016 A | 5/1995 | Low et al. |
| 5,525,337 A | 6/1996 | Willingham et al. |
| 5,646,253 A | 7/1997 | Wallace et al. |
| 5,688,488 A | 11/1997 | Low et al. |
| 5,789,650 A | 8/1998 | Lonberg et al. |
| 5,798,230 A | 8/1998 | Bornkamm et al. |
| 5,817,313 A | 10/1998 | Willingham et al. |
| 5,820,847 A | 10/1998 | Low et al. |
| 5,952,484 A | 9/1999 | Wallace et al. |
| 6,083,502 A | 7/2000 | Pastan et al. |
| 6,124,106 A | 9/2000 | Wallace et al. |
| 6,146,894 A | 11/2000 | Nicolaides et al. |
| 6,153,430 A | 11/2000 | Pastan et al. |
| 6,191,268 B1 | 2/2001 | Liskay et al. |
| 6,261,535 B1 | 7/2001 | Thorpe et al. |
| 6,348,195 B1 | 2/2002 | Wallace et al. |
| 6,365,410 B1 | 4/2002 | Schellenberger et al. |
| 6,602,688 B1 | 8/2003 | Opper et al. |
| 6,808,894 B1 | 10/2004 | Nicolaides et al. |
| 6,809,184 B1 | 10/2004 | Pastan et al. |
| 7,081,518 B1 | 7/2006 | Pastan et al. |
| 7,807,804 B2 | 10/2010 | Sinacore et al. |

(Continued)

FOREIGN PATENT DOCUMENTS

| | | |
|---|---|---|
| EP | 0 197 435 | 7/1992 |
| EP | 0 239 400 | 8/1994 |

(Continued)

OTHER PUBLICATIONS

Alberti, et al., "The CA-MOv18 molecule, a Cell-Surface Marker of Human Ovarian Carcinomas, Is Anchored to the Cell Membrane by Phosphatidylinositol", Biochem. & Biophys. Res. Commun., Sep. 28, 1990, 171(3), 1051-1055.

(Continued)

*Primary Examiner* — Lynn Bristol
(74) *Attorney, Agent, or Firm* — Baker & Hostetler LLP

(57) ABSTRACT

This invention relates to the use of monoclonal and polyclonal antibodies that specifically bind to and have the ability in the alternative to become internalized by cells expressing folate receptor alpha (FRA) and to induce an immune effector activity such as antibody-dependent cellular cytotoxicity. The antibodies are useful in specific delivery of pharmacologic agents to FRA-expressing cells as well as in eliciting an immune-effector activity particularly on tumor cells and precursors. The invention is also related to nucleotides encoding the antibodies of the invention, cells expressing the antibodies; methods of detecting cancer cells; and methods of treating cancer using the antibodies.

12 Claims, 3 Drawing Sheets

(56) References Cited

U.S. PATENT DOCUMENTS

| | | | |
|---|---|---|---|
| 8,124,083 | B2 | 2/2012 | Grasso et al. |
| 9,144,614 | B2 * | 9/2015 | Nicolaides ....... A61K 47/48469 |
| 2002/0192157 | A1 | 12/2002 | Low et al. |
| 2003/0027177 | A1 | 2/2003 | Haseltine et al. |
| 2004/0235108 | A1 | 11/2004 | Grasso et al. |
| 2005/0054048 | A1 | 3/2005 | Grasso et al. |
| 2005/0232919 | A1 | 10/2005 | Grasso et al. |
| 2006/0204506 | A1 | 9/2006 | Ebel et al. |
| 2006/0239910 | A1 | 10/2006 | Nicolaides et al. |
| 2008/0254499 | A1 | 10/2008 | Low et al. |
| 2008/0312093 | A1 | 12/2008 | Inazawa et al. |
| 2009/0081710 | A1 | 3/2009 | Low et al. |
| 2009/0087849 | A1 | 4/2009 | Malinowski et al. |
| 2009/0274697 | A1 | 11/2009 | Grasso et al. |
| 2010/0055034 | A1 | 3/2010 | Martin et al. |
| 2010/0055735 | A1 | 3/2010 | Low et al. |

FOREIGN PATENT DOCUMENTS

| | | |
|---|---|---|
| EP | 1 258 255 | 11/2002 |
| WO | WO 90-07861 | 7/1990 |
| WO | WO 92-07081 | 4/1992 |
| WO | WO 95-24482 | 9/1995 |
| WO | WO 97-25068 | 7/1997 |
| WO | WO 97-42329 | 11/1997 |
| WO | WO 00-73346 | 12/2000 |
| WO | WO 02-37967 | 5/2002 |
| WO | WO 02-054856 | 7/2002 |
| WO | WO 02-094879 | 11/2002 |
| WO | WO 2004-009782 | 1/2004 |
| WO | WO 2004-113388 | 12/2004 |
| WO | WO 2005-011735 | 2/2005 |
| WO | WO 2005-014652 | 2/2005 |
| WO | WO 2005-080431 | 9/2005 |
| WO | WO 2006-116592 | 11/2006 |

OTHER PUBLICATIONS

Almagro, J.C. & Fransson, J., "Humanization of Antibodies", Frontiers in Biosciencs, Jan. 1, 2008; 13,1619-1633.

Alsmadi, et al., "Antibody-Dependent Cellular Cytotoxicity Directed Against Cells Expressing Human Immunodeficiency Virus Type I Envelope of Primary or Laboratory-Adapted Strains by Human and Chimpanzee Monoclonal Antibodies of Different Epitope Specificities", Journal of Viralogy, Jan. 1998, 72(1), 286-293.

Andersson, et al., "Comparisian of the Therapeutic Efficacy of 211At- and 131I-Labelled Monoclonal Antibody MOv18 in Nude Mice With Intraperitoneal Growth of Human Ovarian Cancer", Anticancer Research, Jan.-Feb. 2001, 21(1A), 409-412.

Andersson et al.; "The Curative and Palliative Potential of the Monoclonal Antibody MOv18 Labelled with At in Nude Mice with Intraperitoneally Growing Ovarian Cancer Xenografts"; Acta Oncologica; 2000, 39(6); 741-745.

Armstrong et al., "Efficacy and Safety of Farletuzumab, a Humanized Monoclonal Antibody to Folate Receptor Alpha, in Platinum-Sensitive Relapsed Ovarian Cancer Subjects: Preliminary Data From a Phase-2 Study", Joint ECCO 15-34th ESMO Multidisciplinary Congress, Berlin Sep. 20-24, 2009, Abstract 0-8000.

Armstrong et al., "Exploratory Phase 2 Efficacy Study of MORAb-003, a Monoclonal Antibody Against Folate Receptor Alpha, in Platinum-Sensitive Epithelial Ovarian Cancer in First Relapse", ESMO Slide Presentation, Sep. 23, 2009.

Armstrong et al., "Exploratory Phase II Efficacy Study of MORAb-003, a Monoclonal Antibody Against Folate Receptor Alpha, in Platinum-Sensitive Ovarian Cancer in First Relapse", 2008 ASCO Annual Meeting, Journal Clinical Oncology, 26, 2008, (May 20 suppl; abstr 5500), 2 pages.

ATCC The Essentials of life Science Research for PTA-7552, p. 1, Jan. 27, 2011.

ATCC website search PTA-7552; Dec. 30, 2014, p. 1.

ATCC website search output for PTA-7552.

Ausubel, et al., "Current Protocols in Molecular Biology", John Wiley & Sons, New York, 1998.

Backus, et al., "Folate Depletion Increases Sensitivity of Solid Tumor Cell Lines to 5-Fluorouracil and Antifolates", International Journal of Cancer, Sep. 15, 2000, 87(6), 771-778.

Balint, et al., "Antibody Engineering by Parsimonious Mutagenesis", Gene, Dec. 27, 1993, 137(1), 109-118.

Beckman et al, "Antibody Constructs in Cancer Therapy", American Cancer Society, 109(2), 170-179, Jan. 15, 2007, Published online Dec. 11, 2006.

Beii-McGuinn et al., "A Phase 1 Study of MORAb-003, a Fully Humanized Monoclonal Antibody against Folate Receptor Alpha, in Advanced Epithelial Ovarian Cancer", J Clin Oneal May 20, 2008, 26 (15S), ASCO abstract 5517.

Beii-McGuinn et al., "A Phase 1 Study of MORAb-003, a Fully Humanized Monoclonal Antibody against Folate Receptor Alpha, in Advanced Epithelial Ovarian Cancer", J Clin Oneal, May 20, 2008, 26, suppl, ASCO abstract 5500.

Beii-McGuinn et al., "A Phase 1 Study of MORAb-003, a Fully Humanized Monoclonal Antibody against Folate Receptor Alpha, in Advanced Epithelial Ovarian Cancer", Jun. 20, 2007, ASCO Annual Meeting Proceedings Part I. vol. 25, No. 18S, ASCO abstract 5553.

Beii-McGuinn et al., "A Phase 1 Study of MORAb-003, a Fully Humanized Monoclonal Antibody against Folate Receptor Alpha, in Advanced Epithelial Ovarian Cancer", Jun. 20, 2007, ASCO Annual Meeting Proceedings Part I. vol. 25, No. 18S, ASCO abstract 5583.

Bird, R.E., "Single-Chain Antigen-Binding Proteins", Science, Oct. 21, 1988, 242(4877), 423-442.

Boerman et al., "Comparative Immunohistochemical Study of Four Monoclonal Antibodies Directed Against Ovarian Carcinoma-Associated antigens", International Journal of Gynecological Pathology, 1991, 10(1), 15-25.

Boerner, et al., "Production of Antigen-Specific Human Monoclonal Antibodies From In Vitro-Primed Human Splenocytes", J. of Immunol., Jul. 1, 1991, 147(1), 86-95.

Bolen et al., "The Src Family of Tyrosine Protein Kinases in Hemopoietic Signal Transduction", FASEB, Dec. 1992, 6(15), 3403-3409.

Bottero et al., "Gene Transfection and Expression of the Ovarian Carcinoma Marker Folate Binding Protein on NIH/3T3 Cells Increases Cell Growth In Vitro and In Vivo", Cancer Research, Dec. 1993, 53(23), 5791-5796.

Bowie et al, "Deciphering the Message in Protein Sequences: Tolerance to Amino Acid Substitutions", Science, Mar. 16, 1990, 247(4948), 1306-1310.

Buist et al., "Tumor Uptake of Intravenously Administered Radiolabeled Antibodies in Ovarian Carcinoma Patients in Relation to Antigen Expression and Other Tumor Characteristics", International Journal of Cancer, Apr. 21, 1995, 64(2), 92-98.

Bukowski et al., "The Management of Recurrent Ovarian Cancer", Semin Oneal., Apr. 2007, 34(2 Suppl2), S1-15.

Campbell, et al., "Folate-Binding Protein Is a Marker for Ovarian Cancer", Cancer Res., Oct. 1, 1991, 51(19), 5329-5338.

Cao, et al., "Expression of Novel Markers of Pancreatic Ductal Adenocarcinoma in Pancreatic Nonductal Neoplasms: Additional Evidence of Different Genetic Pathways", Mod. Pathol., Jun. 2005, 18(6), 752-761.

Casalini, et al., "Use of Combination of Monoclonal Antibodies Directed Against Three Distinct Epitopes of a Tumor-Associated Antigen: Analysis of Cell Binding and Internalization", International Journal Cancer, May 10, 1991, 48(2), 284-290.

Cespedes et al., 'Mouse Models in Oncogenisis and Cancer Therapy', Clinical Translation. Oncology, May 2006, (8)5, 318-329.

Chang, et al., "Monoclonal Antibody K1 Reacts With Epithelial Mesothelioma But Not With Lung Adenocarcinoma", American Journal of Surgical Pathology, Mar. 1992, 16(3), 259-268.

Chatterjee et al., "GPI Anchoring Leads to Sphingolipid-Dependent Retention of Endocytosed Proteins in the Recycling Endosomal Compartment", The EMBO Journal, Feb. 2001, 20(7), 1583-1592.

Clynes et al., "Inhibitory Fc Receptors Modulate In Vivo Cytoxicity Against Tumor Targets", Nature Medicine, Apr. 2000, 6(4), 443-446.

(56) References Cited

OTHER PUBLICATIONS

Clynes, et al., "Fe Receptors Are Required in Passive and Active Immunity to Melanoma", Procceedings of the National Academy of Sciences USA, Jan. 20, 1998, 95(2), 652-656.
Cogliati, et al., "Preparation and Biological Characterization of Conjugates Consisting of Ricin and a Tumor-Specific Non-Internalizing MAb", Anticancer Res., Jan.-Feb. 1991, 11(1), 417-421.
Cole, et al., "The EBV-Hybridoma Technique and Its Application to Human Lung Cancer", Monoclonal Antibodies and Cancer Therapy 27, UCLA Symposia on Molecular and Cellular Biology, New Series) (eds. R.A. Reisfeld and S.Sell), 1985, 77-96.
Coleman et al., Farletuzumab, a Novel Monoclonal Antibody Against Folate Receptor-a, Exhibits Clinical Efficacy in Platinum-Snesitive 1st Relapse of Ovarian Cancer Subjects, ESGO Slide presentation poster, Oct. 13, 2009.
Coliva, et al., Cancer Immunol. Immunother., Dec. 2005, Epub: May 31, 2005, 54(12), 1200-1213 (Abstract).
Coney, et al., "Chimeric Murine-Human Antibodies Directed Against Folate Binding Receptor Are Efficient Mediators of Ovarian Carcinoma Cell Killing", Cancer Res., May 1, 1994, 54(9), 2448-2455.
Coney, et al., "Cloning of a Tumor-Associated Antigen: MOV18 and MOV19 Antibodies Recognize a Folate-Binding Protein", Cancer Res., Nov. 15, 1991, 51(22), 6125-6132.
Correa, "Tumor Targeting in Cancer Therapy: Internalization of Antibodies", Humana Press, Totowa, NJ, 21, 391-409.
De Genst et al., "Antibody Repertoire Development in Camelids", Developmental Comparative Immunology, 2006; 30,187-198.
Dennis, C., "Cancer: Off by a Whisker", Nature, Aug. 17, 2006, 442(7104), 739-741.
Ebel, et al., "Preclinical E valuation of MORAb-003, a Humanized Monoclonal Antibody Antagonizing Folate Receptor-Alpha", Cancer Immun., Mar. 9, 2007, 7, 6.
Elit et al., "A Randomized, Double-Blind, Placebo-Controlled Phase II Study of the Efficacy and Safety of Farletuzumab (MORAb-003) in Combination With Weekly Paclitaxel in Subjects With Platinum-Resistant or Refractory Relapsed Ovarian Cancer", 2010 ASCO Annual Meeting, J. Clinical Oncology, 28, 15s, 2010, (suppl; abstr TPS255), 2 pages.
Ellison, et al, "The Nucleotide Sequence of a Human Immunoglobulin Cγ1 Gene", Nucleic Acids Research, 1982 , 10(13), 4071-4079.
Elwood, P. C., "Molecular Cloning and Characterization of the Human Folate-binding protein eDNA from Placenta and Malignant Tissue Culture (KB) Cells", J. Bioi. Chem., Sep. 5, 1989, 264(25), 14893-14901.
Elwood, P.C., et al., "The divergent 5' Termini of the A Human Folate Receptor (Hfr) Mrnas Originate From Two Tissue-Specific Promoters and Alternative Splicing: Characterization of the A hFR Gene Structure", Biochemistry, Feb. 11, 1997, 36(6), 1467-1478.
European Patent Application No. 05722917.1: Examination Report dated Jun. 18, 2012, 8 pages.
Franklin, et al., "New Anti-Lung-Cancer Antibody Cluster 12 Reacts With Human Folate Receptors Present on Adenocarcinoma", Int. J. Cancer, 1994, Suppl. 8, 89-95.
Frigerio, et al., "Assembly, Secretion, and Vacuolar Delivery of a Hybrid Immunoglobulin in Plants", Plant Physiol., Aug. 2000, 123(4), 1483-1493.
Fujimori et al, A Modeling Analysis of Monoclonal Antibody Percolation Through Tumors: A Binding-Site Barrier, Journal Nuclear Medicine, 31, 1191-1198, Jul. 1990.
Fundamental Immunology 242, William E. Paul, M.D., ed., 3rd ed. 1993.
FY2009 Product Creation Meeting, Dramatic Leap Plan 2011, Eisai Co., Ltd., Power Point Presentation, 121 pages, Dec. 18, 2009.
Galmozzi, et al., "Exon 3 of the A Folate Receptor Gene Contains a 5' Splice Site Which Confers Enhanced Ovarian Carcinoma Specific Expression", FEBS Letters, Jul. 27, 2001, 502(1-2), 31-34.
Garcia, A.A., "Salvage Therapy for Ovarian Cancer", Curr. Oneal. Rep., Sep. 1999, 1(1), 64-70.
Garin-Chesa, et al., "Trophoblast and Ovarian Cancer Antigen LK26", Am. J. of Pathol., Feb. 1993, 142(2), 557-567.
Garmestani, et al., "Synthesis and Evaluation of a Macrocyclic Bifunctional Chelating Agent for Use With Bismuth Radionuclides", Nucl. Med. Bioi., May 2001, 28(4), 409-418.
Goldenberg-Furmanov et al., "Lyn Is a Target Gene for Prostate Cancer: Sequence-Based Inhibition Induces Regression of Human Tumor Xenografts", Cancer Research, Feb. 1, 2004, 64(3), 1058-1066.
Gould et al.; "Comparison of IgE and IgG Antibody-Dependent Cytotoxicity In Vitro and in a SCID Mouse Xenograft Model of Ovarian Carcinoma"; Eur. J. Immunol.; 1999; 29; 3527-3537.
Gruner, et al., "The Folate Receptor as a Potential Therapeutic Anticancer Target", Investigational New Drugs, 1999, 16(3), 205-219.
Gussow et al., "Humanization of Monoclonal Antibodies", Methods in Enzymology, 1991, 203, 99-121.
Hanlon, et al., "In vitro Uptake, Anabolism, and Cellular Retention of 1843U89 and Other Benzoquinazoline Inhibitors Ofthymidylate Synthase", Cancer Res., Jul. 15, 1996, 56(14), 3301-3306.
Harkins, K.R., "Antibody Purification Methods", Basic Methods in Antibody Production and Characterization, CRC Press, Howard, G.C., et al. (Eds.), 2000, Chapter 11, 141-168.
Hassan, et al., "Anti-tumor Activity of K1-LysPE38QR, an Immunotoxin Targeting Mesothelin, a Cell-Surface Antigen Overexpressed in Ovarian Cancer and Malignant Mesothelioma", J. of Immunotherapy, Jul.-Aug. 2000, 23(4), 473-479.
Hassan, et al., "Antitumor Activity of SS(dsFv)PE38 and SS1(dsFv)PE38, Recombinant Antimesothelin Immunotoxins Against Human Gynecologic Cancers Grown in Organotypic Culture In Vitro", Clin. Cancer Res., Nov. 2002, 8(11), 3520-3526.
Hassan, et al., "Mesothelin: A New Target for Immunotherapy", Clinical Cancer Research, Jun. 15, 2004, 10(12 pt. 1), 3937-3942.
Hassan, et al., "SS1(dsFv)-PE38 Anti-Mesothelin Immunotoxin in Advanced Malignancies: Phase I and Pharmacokinetic Studies of Alternate-Day Infusion", Proc. Am. Soc. Clin. Oneal., 2002, Abstract No. 113, downloaded from the Internet on Oct. 20, 2005, 2 pages.
Hassan, R., "Targeted Therapy of Mesothelin Expressing Mesotheliomas (MM), Ovarian Cancer (OC) and Pancreatic Cancer (PC)", Journal of Clinical Oncology, 2004, p. 3035 (Abstract).
Helms et al., "Lipids as Targeting Signals: Lipid Rafts and Intracellular Trafficking", Traffic, Apr. 2004, 5(4), 247-254.
Holm, et al., "Characterization of a High-Affinity Folate Receptor in Normal and Malignant Human Testicular Tissue", Bioscience Reports, Dec. 1999, 19(6), 571-580.
Holm, et al., "Folate Receptor of Human Mammary Adenocarcinoma", APMIS, Jun. 1994, 102(6), 413-419.
Holm, et al., "Folate Receptors in Malignant and Benign Tissues of Human Female Genital Tract", Biosci. Reports, Aug. 1997, 17(4), 415-427.
Hough, et al., "Coordinately Up-Regulated Genes in Ovarian Cancer", Cancer Res., May 15, 2001, 61(10), 3869-3876.
Houghton, et al., "Monoclonal Antibodies: Potential Applications to the Treatment of Cancer", Seminars in Oncology, Jun. 1986, 13(2), 165-179.
Howard, et al. (Eds.), "Antibody Purification Methods", Basic Methods in Antibody Production and Characterization, CRC Press, 2000, Chapter 11, 142-168.
Huang, et al., "Construction of Representative Immunoglobulin Variable Region Edna Libraries From Human Peripheral Blood Lymphocytes Without In Vitro Stimulation", J. of Immunol. Methods, 1991, 141, 227-236.
Huang, et al., "On Global Sequence Alignment", CABIOS, Jun. 1994, 10(3), 227-235.
Hudson, P.J., "Recombinant Antibody Constructs in Cancer Therapy", Curr. Opin. Immunol., Oct. 1999, 11(5), 548-557.
Huston, et al., "Protein Engineering of Antibody Binding Sites: Recovery of Specific Activity in an Anti-Digoxin Single-Chain Fv Analogue Produced in *Escherichia coli*", Proc. Natl. Acad. Sci. USA, Aug. 1988, 85(16), 5879-5883.
Jackman, et al., "Cellular Pharmacology and In Vivo Activity of a New Anticancer Agent, ZD9331: A Water-Soluble,

(56) References Cited

OTHER PUBLICATIONS

Nonpolygluamatable, Quinazoline-Based Inhibitor of Thymidylate Synthase", Clinical Cancer Research, Jun. 1997, 3(6), 911-921.
Jackman, et al., "ICI D1694, a Quinazoline Antifolate Thymidylate Synthase Inhibitor That Is a Potent Inhibitor of L1210 Tumor Cell Growth In Vitro and In Vivo: A New Agent for Clinical Study", Cancer Research, Oct. 15, 1991, 51(20), 5579-5586.
Jemal et al. "Cancer Statistics 2008", CA Cancer J Clin, Mar.-Apr. 2008, 58(2), 71-96, epublished Feb. 20, 2008.
Johnston, S.R., "Ovarian Cancer: Review of the National Institute for Clinical Excellence (NICE) Guidance Recommendations", Cancer Invest., Dec. 2004, 22(5), 730-742.
Jones, P.T., et al., "Replacing the Complementarity-Determining Regions in a Human Antibody With Those From a Mouse", Nature, May 29-Jun. 4, 1986, 321(6069), 522-525.
Kalli et al., "Folate Receptor Alpha as a Tumor Target in Epithelial Ovarian Cancer", Gynecol Oneal., Mar. 2008, 108(3), 619-626.
Kanner et al., "Farletuzumab, a Humanized Monoclonal Antibody Against Folate Receptor a, in Epithelial Ovarian Cancer: a Phase I Study", Clinical Cancer Research, Nov. 1, 2010, 16(21), 5288-5295.
Kaufman, et al. (Eds.), Handbook of Molecular and Cellular Methods in Biology and Medicine, CRC Press, Boca Raton, 1995.
Keepers, et al., "Comparison of the Sulforhodamine B Protein and Tetrazolium (MTT) Assays for In Vitro Chemosensitivity Testing", Eur. J. of Cancer, 1991, 27(7), 897-900.
Keleman, "The Role of Folate Receptor Alpha in Cancer Development, Progression and Treatment: Cause, Consequence or Innocent Bystander", Int J Cancer, Jul. 15, 2006, 119(2), 243-250.
Khazaeli, et al., "Human Immune Response to Monoclonal Antibodies", J Immunother Emphasis Tumor Immunol., Jan. 1994, 15(1), 42-52.
Kikuchi, et al., "Apoptosis Inducing Bivalent Single-Chain Antibody Fragments Against CD47 Showed Antitumor Potency for Multiple Myeloma", Leuk. Res., Apr. 2005, Epub: Dec. 18, 2004, 29(4), 445-450.
Kohler, et al., "Continuous Cultures of Fused Cells Secreting Antibody of Predefined Specificity", Nature, Aug. 7, 1975, 256(5517), 495-497.
Kontermann, et al. (Eds.), Antibody Engineering (Springer Lab Manual), Springer-Verlag, 2001.
Kozbor, et al., "The Production of Monoclonal Antibodies From Human Lymphocytes", Immunol. Today, 1983, 4(3), 72-79.
Kreitman, et al., "Immunotoxins for Targeted Cancer Therapy", Adv. Drug Del. Rev., Apr. 6, 1998, 31(1-2), 53-88.
Kusano, et al., "Immunocytochemical Study on Internalization of Anti-Carbohydrate Monoclonal Antibodies", Anticancer Res., Nov.-Dec. 1993, 13(6A), 2207-2212.
Kyriakos, et al., "The Fate of Antibodies Bound to the Surface of Tumor Cells In Vitro", Cancer Res., Feb. 15, 1992, 52(4), 835-842.
Lacey, et al., "Complementary DNA for the Folate Binding Protein Correctly Predicts Anchoring to the Membrane by Glycosyi-Phosphatidylinositol", J. Clin. Invest, Aug. 1989, 84(2), 715-720.
Leamon et al., "Delivery of Macromolecules Into Living Cells: A Method That Exploits Folate Receptor Endocytosis", Proc Natl Acad Sci USA, Jul. 1991, 88913, 5572-5576.
Lear et al. "Improved Tumor Imaging With Radiolabeled Monoclonal Antibodies by Plasma Clearance of Unbound Antibody With Anti-Antibody Column", Radiology, May 1991, 179(2), 509-512.
Li, et al., "Cytotoxic Activity of the Recombinant Anti-Mesothelin Immunotoxin, SS1 (dsFv) PE38, Towards Tumor Cell Lines Established From Ascites of Patients With Peritoneal Mesotheliomas", Anticancer Res., May-Jun. 2004, 24(3A), 1327-1335.
Little, et al., "Of Mice and Men: Hybridoma and Recombinant Antibodies", Immunol. Today, Aug. 2000, 21(8), 364-370.
Ingley, "Src Family Kinases: Regulation of Their Activities, levels and Identification of New Pathways", BBA, Jan. 2008, 1784(1), 56-65.
Markman et al., "Phase II Trial of Weekly Paclitaxel (80 mg/m2) in Platinum and Paclitaxel-Resistant Ovarian and Primary Peritoneal Cancers: A Gynecologic Oncology Group study", Gynecologic Oncology, Jun. 2006, 101(3), 436-440.
Marks, et al., "By-passing immunization. Human antibodies from V-gene Libraries Displayed on Phage", J. Mol. Bioi., Dec. 5, 1991, 222(3), 581-597.
Maziarz, et al., "Complete Mapping of Divergent Amino Acids Responsible for Differential Ligand Binding of Folate Receptors a and 13", J. Bioi. Chem., Apr. 16, 1999, 274(16), 11066-11091.
McCall, et al., "Increasing the Affinity for Tumor Antigen Enhances Bispecific Antibody Cytotoxicity", J. of Immunol., May 15, 2001, 166(10), 6112-6117.
McPherson, (Ed.), Directed Mutagenesis: A Practical Approach, IRL Press, Oxford, 1991.
Miotti et al., "Interaction of Folate Receptor With Signaling Molecules Lyn and Ga13 in Detergent-Resistant Complexes From the Ovary Carcinoma Cell Lines", J Cell Sci, Jan. 2000, 113(pt 2), 349-357.
Miotti, et al., "Characterization of Human Ovarian Carcinoma-Associated Antigens Defined by Novel Monoclonal Antibodies With Tumor-Restricted Specificity", Int. J. Cancer, Mar. 15, 1987, 39(3), 297-303.
Molthoff, et al., "Experimental and Clinical Analysis of the Characteristics of a Chimeric Monoclonal Antibody, MOv18, Reactive with an Ovarian Cancer-Associated Antigen", J Nucl Med., Nov. 1992, 33(11), 2000-2005.
Morphotek, "Morphotek Announces Top-Line Results of a Phase III Study of Farletuzumab in Patients With Relapsed Platinum-Sensitive Epithelial Ovarian Cancer", Exton, PA, Jan. 10, 2013, Press Release, p. 1.
Morrison, et al., "Chimeric Human Antibody Molecules: Mouse Antigen-Binding Domains With Human Constant Region Domains", Proc. Natl. Acad. Sci. USA, Nov. 1984, 81(21), 6851-6855.
Nahta et al., "Growth Factor Receptors in Breast Cancer: Potential for Therapeutic Intervention", Oncologist, Feb. 2003, 8(1), 5-17.
Nelson et al., "51Cr Release Assay of Antibody-Dependent Cell-Mediated Cytotoxicity (ADCC)", Current Protocols in Immunol., May 2001, Chapter 7, Unit 7.27-7.27.8, 8 pages.
Nicolaides, et al., "Analysis of the 5' region of PMS2 Reveals Heterogeneous Transcripts and a Novel Overlapping Gene", Genomics, Sep. 20, 1995, 29(2), 329-334.
Niwa, et al., "Defucosylated Chimeric Anti-CC Chemokine Receptor 4 IgG1 With Enhanced Antibody-Dependent Cellular Cytotoxicity Shows Potent Therapeutic Activity to T-Cellleukemia and Lymphoma", Cancer Res., Mar. 15, 2004, 64(6), 2127-2133.
Ordonez, N.G., "Application of Mesothelin Immunostaining in Tumor Diagnosis", Am. J. Surg. Pathol., Nov. 2003, 27(11), 1418-1428.
Orlandi, et al., "Cloning Immunoglobulin Variable Domains for Expression by the Polymerase Chain Reaction", Proc. Natl. Acad. Sci. USA, May 1989, 86(10), 3833-3837.
Ozols et al., "No Title", Seminars in Oncology, Apr. 2006, 33(s Suppl 6), S1-S2 Johnston, S.R., "Ovarian cancer: review of the National Institute for Clinical Excellence (NICE) guidance recommendations", Cancer Invest., Dec. 2004, 22(5), 730-742.
Ozols et al., "Systemic Therapy for Ovarian Cancer: Current Status and New Treatments", Semin Oneal., Apr. 2006, 33(2 Suppl 6), S3-S11.
Parsons, R., et al., "Mismatch Repair Deficiency in Phenotypically Normal Human Cells", Science, May 5, 1995, 268(5211), 738-740.
Parsons et al., "Src Family Kinases, Key Regulators of Signal Transduction", Oncogene, Oct. 28, 2004, 23(48), 7906-7909.
Paul, et al., "Selection of Tumor-Specific Internalizing Human Antibodies From Phage Libraries", J. of Molecular Bioi., Sep. 1, 2000, 301(5), 1149-1161.
Peoples, G.E., et al., "Vaccine Implications of Folate Binding Protein, a Novel Cytotoxic T Lymphocyte-Recognized Antigen System in Epithelial Cancers", Clinical Cancer Res., Dec. 1999, 5(12), 4214-4223.
Persson, et al., "Generation of Diverse High-Affinity Human Monoclonal Antibodies by Repertoire Cloning", Proc. Nat. Acad. Sci. USA, Mar. 15, 1991, 88(6), 2432-2436.

(56) References Cited

OTHER PUBLICATIONS

Peters, et al., "Transformation of Mouse Fibroblasts With the Oncogenes H-ras OR trk Is Associated With Pronounced Changes in Drug Sensitivity and Metabolism", Int. J. of Cancer, May 28, 1993, 54(3), 450-455.
Potamianou et al, Oncology, 2005; 69(4), 348-353, Abstract.
Presta, L. G., "Antibody Engineering", Curr. Op. Biotechnol., Aug. 1992, 3(4), 394-398.
Queen, et al., "A Humanized Antibody That Binds to the Interleukin 2 Receptor", Proc. Nat. Acad. Sci. USA, Dec. 1989, 86(24), 10029-10033.
Rafi, et al., "Preclinical and Phase I Clinical Studies With the Nonclassical Antifolate Thymidylate Synthase Inhibitor Nolatrexed Dihydrochloride Given by Prolonged Administration in Patients With Solid Tumors", J. of Clin. Oneal., Mar. 1998, 16(3), 1131-1141.
Reichmann, et al., "Reshaping Human Antibodies for Therapy", Nature, Mar. 1988, 332(6162), 323-327.
Rettig, et al., "Cell-surface Glycoproteins of Human Sarcomas: Differential Expression in Normal and Malignant Tissues and Cultured Cells", Proc. Natl. Acad. Sci. USA, May 1988, 85(9), 3110-3114.
Rhee, et al., "Biochemical Studies on PT523, a Potent Nonpolyglutamatable Antifolate, in Cultured Cells", Mol. Pharmacal., Apr. 1994, 45(4), 783-791.
Ripani, et al., "Human Trop-2 Is a Tumor-Associated Calcium Signal Transducer", Int. J. Cancer, May 29, 1998, 76(5), 671-676, (Abstract).
Rosowsky, A., "PT523 and Other Aminopterin Analogs With a Hemiphthaloyi-L-Ornithine Side Chain: Exceptionally Tight-Binding Inhibitors of Dihydrofolate Reductase Which Are Transported by the Reduced Folate Carrier but Cannot Form Polyglutamates", Curr. Med. Chem., Apr. 1999, 6(4), 329-352.
Ross, et al., "Antibody-Based Therapeutics in Oncology", Exp. Rev. Anticancer Ther., Feb. 2003, 3(1), 107-121.
Ross, et al., "Differential Regulation of Folate Receptor Isoforms in Normal and Malignant Tissues In Vivo and in Established Cell Lines", Cancer, May 1, 1994, 73(9), 2432-2443.
Rudikoff et al, "Single Amino Acid Substitution Altering Antigen-Binding Specificity", PNAS, USA, Mar. 1982, 79(6), 1979-1983.
Rudnick et al, "Affinity and Avidity in Antibody-Based Tumor Targeting", Cancer Biotherapy and Radiopharmaceuticals, 24(2), 155-162, Apr. 2009.
Sadasivan, et al., "Purification, Properties, and Immunological Characterization of Folate-Binding Proteins From Human Leukemia Cells", Biochim. et Biophys. Acta, Jul. 16, 1987, 925(1), 36-47.
Sandhu, "Protein Engineering of Antibodies", Critical Reviews Biotechnology, 1992, 12(5-6),437-62, Published Online: Sep. 1992.
Sambrook, et al., Molecular Cloning: A Laboratory Manual, 2nd Ed., Cold Spring Harbor Laboratory Press, Plainview, New York, 1989.
Scholler, et al., "Soluble member(s) of the Mesothelin/ Megakaryocyte Potentiating Factor Family Are Detectable in Sera From Patients With Ovarian Carcinoma", Proc. Natl. Acad. Sci. USA, Sep. 28, 1999, 96(20), 11531-11536.
Scholl et al., "Folic Acid: Influence on the Outcome of Pregnancy", The American Journal of Clinical Nutrition, May 2000, 71(5 Supplement), 1295S-1303S.
Scott, et al., "Immunological effects of chimeric anti-GD3 Monoclonal Antibody KM871 in Patients With Metastatic Melanoma", Cancer Immun., Feb. 22, 2005, 5(3), 1-12.
Shen, et al., "Expression Levels of Functional Folate Receptors Alpha and Beta Are Related to the Number of N-Glycosylated Sites", Biochem J. Nov. 1, 1997, 327(Pt. 3), 759-764.
Shewach, et al., "Radiosensitization of Human Tumor Cells by Gemcitabine In Vitro", Semin. Oncol., Aug. 1995, 22(2 Suppl 11), 68-71.
Shields, et al., "Anti-IgE Monoclonal Antibodies That Inhibit Allergen-Specific Histamine Release", Int. Arch. Allergy Immunol., May-Jun. 1995, 107(1-3), 412-413.

Shields, et al., "High Resolution Mapping of the Binding Site on Human IgG1 for FcgammaRI, FcgammaRII, FcgammaRIII, and FeRn and Design of IgG1 Variants With Improved Binding to the FcgammaR", J. of Biological Chem., Mar. 2, 200, Epub: Nov. 28, 2000, 276(9), 6591-6604.
Shih, et al., "LY231514, a pyrrolo[2,3-d]pyrimidine-Based Antifolate That Inhibits Multiple Folate-Requiring Enzymes", Cancer Res., Mar. 15, 1997, 57(6), 1116-1123.
Shinkawa, et al., "The Absence of Fucose but Not the Presence of Galactose or Bisecting N-Acetylglucosamine of Human IgG1 Complex-Type Oligosaccharides Shows the Critical Role of Enhancing Antibody-Dependent Cellular Cytotoxicity", J. Biological Chem., Jan. 31, 2003, Epub: Nov. 8, 2002, 278(5), 3466-3473.
Skerra, et al., "Assembly of a Functional Immunoglobulin Fv Fragment in *Escherichia coli*", Science, May 20, 1988, 240(4855), 1038-1041.
Smith-Jones et al., "Preclinical Radioimmunotargeting of Folate Receptor Alpha Using the Monoclonal Antibody Conjugate DOTA-MORAb-003", Nucl Med Bioi, Apr. 2008, 35(3), 343-351.
Spannuth et al., "Farletuzumba in Epithelial Ovarian Carcinoma", Expert Opinion on Biological Therapy, Mar. 2010, 10(3), 431-437.
Spannuth et al., "Therapeutic Eficacy of Folate Receptor a blockade with MORAb-003 in Ovarian Cancer", Gynecologic Oncology, 2008, Abstracts, 108(3S), S135.
Strome et al., "A Mechanistic Perspective of Monoclonal Antibodies in Cancer Therapy Beyond Target-Related Effects", Oncologist, Sep. 2007, 12(9), 1084-1095.
Sudimack, et al., "Targeted Drug Delivery via the Folate Receptor", Adv. Drug Deliv. Rev., Mar. 30, 2000, 41(2), 147-162.
Suzuki et al., "GPI-Anchored Receptor Clusters Transiently Recruit Lyn and Ga for Temporary Cluster I mmobilization and Lyn Activation: Single-Molecule Tracking Study 1", JCB Article, May 21, 2007, 177(4), 717-730.
Talmadge et al., 'Murine Models to Evaluate Novel and Conventional Therapeutic Strategies for Cancer', The American Journal of Pathology, Mar. 2007, 170(3), 793-804.
Taylor, et al., "A dideazatetrahydrofolate analogue lacking a chiral center at C-6,-[4[2-(2-amino-3,4-dihydro-4-ox-7H-pyrrolo[2,3-d]pyrimidin-5-yl)ethyl]benzoyi]-L-glutamic acid, Is an Inhibitor of Thymidylate Synthase", J. Med. Chem., Nov. 13, 1992, 35(23), 4450-4454.
Tempest, et al., "Reshaping a Human Monoclonal Antibody to Inhibit Human Respiratory Syncytial Virus Infection In Vivo", Biotechnology, Mar. 1991, 9(3), 266-271.
Thurber et al, "Antibody Tumor Penetration: Transport Opposed by Systemic and Antigen-Mediated Clearance", Advanced Drug Delivery Reviews, 60(12),1421-1434, Sep. 2008.
Tibben et al., 'Pharmacokinetics, Biodistribution and Biological Effects of Intravenously Administered Bispecific Monoclonal Antibody OC/TR F(ab')2 in Ovarian Carcinoma Patients', Int. J. Cancer, May 16, 1996, 66(4), 477-486, (Abstract only).
Titani, et al., "The Amino Acid Sequence of α K Type Bence-Jones Protein", The Journal of Biological Chemistry, Jul. 1969, 244(13), 3550-3560.
Toffoli et al, "Resistance to Methotrexate in SKOV-3 Cell Lines After Chronic Exposure to Carbamazepine is Associated with a Decreased Expression of Folate Receptor", International Journal of Cancer, 85, 683-690, Mar. 1, 2000.
Toffoli et al., "Overexpression of Folate Binding Protein in Ovarian Cancers", Int J Cancer, Apr. 1997, 74(2), 193-198.
Tomassetti, et al., "Isolation and Biochemical Characterization of the Soluble and Membrane Forms of Folate Binding Protein Expressed in the Ovarian Carcinoma Cell Line IGOV1", FEBS Letters., Feb. 8, 1993, 317(1-2), 143-146.
van Zanten et al., "Cellular and Humoral Responses After Multiple Injections of Unconjugated Chimeric Monoclonal Antibody MOv18 in Ovarian Cancer Patients: A Pilot Study", J. Cancer Res. Clin. Oneal., Sep. 2002, 128(9), 484-492.
VanZanten-Przybysz, et al., "Influence of the Route of Administration on Targeting of Ovarian Cancer With the Chimeric Monoclonal Antibody MOV18: I.V. VS. I.P.", Int. J. of Cancer, Apr. 1, 2001, 92(1), 106-114.

(56) References Cited

OTHER PUBLICATIONS

Veggian, et al., "Immunohistochemical Reactivity of a Monoclonal Antibody Prepared Against Human Ovarian Carcinoma on Normal and Pathological Female Genital Tissues", Tumori, Oct. 31, 1989, 75(5), 510-513.

Velders, et al., "The Impact of Antigen Density and Antibody Affinity on Antibody-Dependent Cellular Cytotoxicity: Relevance for Immunotherapy of Carcinomas", B. J. Cancer, Aug. 1998, 78(4), 478-483.

Verhoeyen, et al., "Reshaping Human Antibodies: Grafting an Antilysozyme Activity", Science, Mar. 25, 1988, 239(4847), 1534-1536.

Voskoglou-nomikos et al., 'Clinical Predictive Value of the In Vitro Cell Line, Human Xenograft, and Mouse Allograft Preclinical Cancer Models', Clinical Cancer Research, Sep. 15, 2003, 9(11), 4227-4239.

Ward, et al., "Binding Activities of a Repertoire of Single Immunoglobulin Variable Domains Secreted From *Escherichia coli*", Nature, Oct. 12, 1989, 341(2642), 544-546.

Webber, et al., "AG337, a Novel Lipophilic Thymidylate Synthase Inhibitor: In Vitro and In Vivo Preclinical Studies", Cancer Chemother. Pharmacal., 1996, 37(6), 509-517.

Wallace, "Second Conference on Industrial Immunology", "Humanized Antibodies Specific for Human Cancers", ICHEME—Industriallmmunology, a two-day symposium organized by the Institutuion of Chemical Engineers on behalf of the British Coordinating Committee for Biotechnology, and held in Brighton, UK, Jul. 4-5, 1994, 6 pages.

Weitman, et al., "Distribution of the Folate Receptor GP38 in Normal and Malignant Cell Lines and Tissues", Cancer Res., Jun. 15, 1992, 52(12), 3396-3401.

Wolff, et al., "Monoclonal Antibody Homodimers: Enhanced Anti-tumor Activity in Nude Mice", Cancer Res., Jun. 1, 1993, 53(11), 2560-2565.

Wu et al., "Expression of Folate Receptor Type a in Relation to Cell Type, Malignancy, and Differentiation in Ovary, Uterus, and Cervix", Cancer Epidemiology, Biomarkers and Prevention, Sep. 1999, 8(9), 775-782.

Yamaguchi, et al., "A Novel Cytokine Exhibiting Megakaryocyte Potentiating Activity From a Human Pancreatic Tumor Cell Line HPC-Y5", J. Bioi. Chem., Jan. 14, 1994, 269(2), 805-808.

Yang, et al., "Eradication of Established Tumors by a Fully Human Monoclonal Antibody to the Epidermal Growth Factor Receptor Without Concomitant Chemotherapy", Cancer Research, Mar. 15, 1999, 59(6), 1236-1243.

Zafiropoulos, et al., "Induction of Antigen-Specific Isotype Switching by In Vitro Immunization of Human Na"Lve B lymphocytes", Journal of Immunological Methods, Jan. 15, 1997, 200(1-2), 181-190.

Zhang et al., "ErbB Receptors: From Oncogenes to Targeted Cancer Therapies", The Journal of Clinical Investigation, Aug. 2007, 117(8), 2051-2058.

Zola, Monoclonal Antibodies: Preparation and Use of Monoclonal Antibodies and Engineered Antibody Derivatives (Basics: From Background to Bench), Springer-Verlag Ltd., New York, 2000.

Canevar, et al., "Ovarian Carcinoma Therapy with Monoclonal Antibodies", Hybridoma, 1993, 12(5), pp. 501-507.

\* cited by examiner

Igrov-1=hum. Ovarian tumor cells expressing FR
H226=hum. Lung tumor cells negative for FR

ANTIBODIES WITH IMMUNE EFFECTOR ACTIVITY AND THAT INTERNALIZE IN FOLATE RECEPTOR ALPHA-POSITIVE CELLS

CROSS-REFERENCE TO RELATED APPLICATION

This application is a continuation application of U.S. application Ser. No. 13/356,724, filed Jan. 24, 2012, now U.S. Pat. No. 9,144,614, which is a continuation of U.S. application Ser. No. 12/503,983, filed Jul. 16, 2009, now U.S. Pat. No. 8,124,083, which is a divisional application of U.S. application Ser. No. 11/410,442, filed Apr. 24, 2006, now abandoned, which claims benefit of U.S. Provisional Application 60/674,185, filed Apr. 22, 2005. Each of these applications is incorporated herein by reference in its entirety.

TECHNICAL FIELD

This invention relates to the use of monoclonal and polyclonal antibodies that specifically bind to and alternatively become internalized by cells expressing or bearing folate receptor alpha (FRA) ("FRA-positive cells") and induce an immune effector activity such as antibody dependent cellular cytotoxicity. The antibodies are useful in specific delivery of pharmacologic agents to FRA-positive cells as well as in eliciting an immune-effector activity particularly on tumor and dysplastic cells. The invention is also related to cells expressing the monoclonal antibodies, polyclonal antibodies, antibody derivatives, such as chimeric and humanized monoclonal antibodies, antibody fragments, methods of detecting FRA-positive cells, and methods of treating cancer using the antibodies of the invention.

BACKGROUND

There are three major isoforms of the human membrane folate binding proteins, α, β, and γ. The α and β isoforms have about 70% amino acid sequence homology and differ dramatically in their stereospecificity for some folates. Both isoforms are expressed in both fetal and adult tissue, although normal tissue generally expresses low to moderate amounts of FR-β. FR-α, however, is expressed in a subset of normal epithelial cells, and is frequently strikingly elevated in a variety of carcinomas (Ross et al. (1994) *Cancer* 73(9):2432-2443; Rettig et al. (1988) *Proc. Natl. Acad. Sci. USA* 85:3110-3114; Campbell et al. (1991) *Cancer Res.* 51:5329-5338; Coney et al. (1991) *Cancer Res.* 51:6125-6132; Weitman et al. (1992) *Cancer Res.* 52:3396-3401; Garin-Chesa et al. (1993) *Am. J. Pathol.* 142:557-567; Holm et al. (1994) *APMIS* 102:413-419; Franklin et al. (1994) *Int. J. Cancer* 8 (Suppl.):89-95; Miotti et al. (1987) *Int. J. Cancer* 39:297-303; and Vegglan et al. (1989) *Tumori* 75:510-513). FR-α is overexpressed in greater than 90% of ovarian carcinomas (Sudimack and Lee (2000) *Adv. Drug Deliv. Rev.* 41(2):147-62). In addition, it is also over-expressed in a number of other cancers such as but not limited to breast, colorectal, renal, and lung cancer.

In 1987, Miotti et al. described three new monoclonal antibodies that recognized antigens on human ovarian carcinoma cells (Miotti et al. (1987) *Int. J. Cancer* 39(3):297-303). One of these was designated MOv18, which recognizes a 38 kDa protein on the surface of choriocarcinoma cells. MOv18 is a murine, IgG1, kappa antibody and mediates specific cell lysis of the ovarian carcinoma cell line, IGROV1. Alberti et al. ((1990) *Biochem. Biophys. Res. Commun.* 171(3):1051-1055) showed that the antigen recognized by MOv18 was a GPI-linked protein. This was subsequently identified as the human folate binding protein (Coney et al. (1991) *Cancer Res.* 51(22):6125-6132). Tomassetti et al. showed that MOv18 recognizes a soluble form and a GPI-anchored form of the folate binding protein in IGROV1 cells (Tomassetti et al. (1993) *FEBS Lett.* 317(1-2):143-146). Subsequent work combined the variable regions of the mouse MOv18 with human IgG1 (kappa) constant region to create a chimerized MOv18 antibody. The chimerized antibody mediated higher and more specific lysis of IGROV1 cells at 10-100 fold lower antibody concentrations (Coney et al. (1994) *Cancer Res.* 54(9):2448-2455).

U.S. Pat. No. 5,952,484 describes a humanized antibody that binds to a 38 kDa protein (FR-α). The antibody was named LK26, after the antigen by the same name. The original mouse monoclonal antibody was described by Rettig in European Patent Application No. 86104170.5 (published as EP0197435 and issued in the U.S. as U.S. Pat. No. 4,851,332).

Ovarian cancer is the major cause of death due to gynecological malignancy. Although chemotherapy is the recommended treatment and has enjoyed some success, the 5-year survival term is still less than 40%.

A difficult problem in treating ovarian cancer as well as other cancers with cytotoxic drugs is that often the cytotoxin causes toxicity to normal tissues as well as cancerous tissues. An approach to get better specificity to treat cancer is the use of antibodies that can target specific antigens expressed in cancer cells that are not expressed or are expressed at a lower level on normal cells. These targets can be exploited using antibodies to kill antigen-bearing tumors by inhibiting the biological activity of the antigen, eliciting an immune effector function by complement dependent cytotoxicity (CDC) and/or antibody dependent cellular cytotoxicity (ADCC); or by delivering immuno- or radio-conjugates that when delivered to the antigen-bearing cells, specifically kill the target cell. Finding antibodies that can specifically bind to and effectively kill antigen-bearing tumor cells has proven difficult for many cancers. This has been due in part to the inability to obtain robust killing due to lack of immune-effector function or to lack of efficient internalization of antibodies carrying immunotoxins. FRA offers an opportunity to get tumor-specific targeting for several cancer types including ovarian, renal, colorectal and lung cancer.

Provided herein are in-out anti-FRA antibodies that can in the alternative (i.e., have the ability to do both but only one at a time) elicit a robust immune-effector function on and internalize in FRA-positive cells, for example, for delivering toxic conjugates to FRA-positive cells. The antibodies of the invention are effective therapies for cancers that bear FRA such as but not limited to ovarian, renal, colorectal, breast and lung cancers.

SUMMARY OF THE INVENTION

Provided herein are FRA-specific antibodies that alternatively elicit a robust immune-effector function yet are able to internalize in FRA-positive cells, referred to here as in-out anti-FRA antibodies. As used herein, "in-out antibodies" ("in-out Abs") refer to antibodies that can alternatively elicit an immune effector activity and internalize within an antigen-presenting cell by binding to target antigen. Without wishing to be bound by any particular theory, it is believed that in-out Abs bind to the cell surface of an antigen-bearing cell and internalize after a period of time unless engaged by immune-effector cells or biochemicals that are recruited to the antigen-antibody-bearing cell. Antibodies that are able to elicit an immune effector effect such ADCC or CDC and internalize have been previously described (Wolff et al. Monoclonal antibody homodimers: enhanced antitumor activity in nude mice. *Cancer Res.* 1993 Jun. 1; 53:2560-5), however, it is not obvious that in-out antibodies can be developed against any antigen or epitope (Kusano et al. Immunocytochemical study on internalization of anti-carbohydrate monoclonal antibodies. *Anticancer Res.* 1993 November-December; 13(6A):2207-12). In-out antibodies that can target FRA have not been described previously. FRA-specific antibodies have been previously described but such antibodies are not known to internalize upon binding to the antigen (Cogliati et al. Preparation and biological characterization of conjugates consisting of ricin and a tumor-specific non-internalizing MAb. *Anticancer Res.* 11:417-21, 1991). Antibodies that can target cell surface antigens do not always elicit an immune effector function upon binding to the cell surface antigen (Niwa et al. Defucosylated chimeric anti-CC chemokine receptor 4 IgG1 with enhanced antibody-dependent cellular cytotoxicity shows potent therapeutic activity to T-cell leukemia and lymphoma. *Cancer Res.* 64:2127-33, 2004; Kikuchi et al. Apoptosis inducing bivalent single-chain antibody fragments against CD47 showed antitumor potency for multiple myeloma. *Leuk. Res.* 29:445-50, 2005; Scott et al Immunological effects of chimeric anti-GD3 monoclonal antibody KM871 in patients with metastatic melanoma. *Cancer Immun.* February 22; 5:3, 2005). Provided herein are antibodies that bind to the cell surface antigen FRA and, in the alternative, elicit an immune effector activity (such as ADCC or CDC) and internalize within antigen-positive cells. These antibodies and derivatives thereof are useful for cancer therapy.

The invention provides in-out antibodies that specifically bind to FRA. In some embodiments, the antibodies bind antigen with greater affinity and/or avidity than LK26 and MOv18. In some embodiments the in-out antibodies of the invention bind the same epitope, for example a conformational epitope, as that bound by LK26 or MOv18. In other embodiments, the in-out antibodies of the invention bind a different epitope as that bound by LK26 or MOv18.

The antibodies of the invention may be chimeric, including, but not limited to a human-mouse chimeric antibodies. The antibodies of the invention may also be humanized. The antibodies of the invention may also be fully human. The invention also provides: hybridoma cells that express the antibodies of the invention; polynucleotides that encode the antibodies of the invention; vectors comprising the polynucleotides that encode the antibodies of the invention; and expression cells comprising the polynucleotides of the invention, referred to as transfectomas.

The invention also provides methods of producing in-out antibodies of the invention. Some methods comprise the step of culturing the transfectoma or hybridoma cell that expresses an antibody of the invention. The antibody-producing cells of the invention may be bacterial, yeast, insect cells, and animal cells, preferably, mammalian cells.

The invention further provides methods of inhibiting the growth of FRA-positive cells such as dysplastic or tumor cells associated with increased expression of FRA. In some embodiments, such methods comprise administering to a patient with FRA-positive cells a composition comprising an in-out antibody of the invention. The methods may be used for the treatment of various dysplastic conditions, such as, but not limited to ovarian, breast, colorectal, renal and lung cancer. In preferred embodiments, the patients are human patients. In some embodiments, the antibodies are conjugated to one or more chemotherapeutic agents such as, but not limited to radionuclides, toxins, and cytotoxic or cytostatic agents. In other embodiments the antibodies are used in combination with one or more chemotherapeutic agents or biomolecules. Yet in other embodiments the antibodies are used in combination with an antifolate compound. In-out antibodies can be administered as a single agent, as a conjugated or unconjugated antibody, or in combination with the conjugated or unconjugated forms or another therapeutic agent.

Previous attempts to develop therapeutic antibodies that specifically target FRA have been performed with little success due to poor internalization and/or affinity such as the MOv18 antibody (Cogliati et al. Preparation and biological characterization of conjugates consisting of ricin and a tumor-specific non-internalizing MAb. *Anticancer Res.* 11:417-21, 1991). This lack of internalization could be due to low affinity or poor internalization due to antibody composition and/or epitope binding. In addition, the MOvl 8 antibody was attempted as an immunoconjugate because the unconjugated form was not cytotoxic itself. Provided herein are in-out antibodies that alternatively internalize in FRA-positive cells and elicit a cytotoxic effect via an immune effector activity.

Other features and advantages of the invention will be apparent from the detailed description and examples that follow.

BRIEF DESCRIPTION OF THE DRAWINGS

FIG. 1A demonstrates FRA-specific antibodies that have in-out activity (ML-1). Shown is an ELISA identifying antibody that can specifically bind to various amounts of recombinant FRA antigen. ELISAs also can be formatted using purified, semi-purified, membrane preps or whole cells expressing FRA. FIG. 1B shows the results of FACS analysis of ML-1 binding to FRA-expressing cells (IGROV-1) while no binding is observed on FRA-null H226 cells. These data were confirmed by western blot analysis.

FIG. 3 shows the ability of ML-1 linked to saporin (diamond) to kill cells in contrast to ML-1 unconjugated (square) while an isotype control antibody MORAb-A92 did not kill cells in conjugated or unconjugated toxin form (triangle and X, respectively). As control, cells not expressing FRA were used and found that ML-1 has no toxic effect in toxin-conjugated or unconjugated form (not shown). These data support the finding that ML-1 internalizes in FRA-bearing cells. Data is evaluated by comparing treated and untreated wells and results are expressed as percent of control.

DETAILED DESCRIPTION OF ILLUSTRATIVE EMBODIMENTS

Figure 1A:
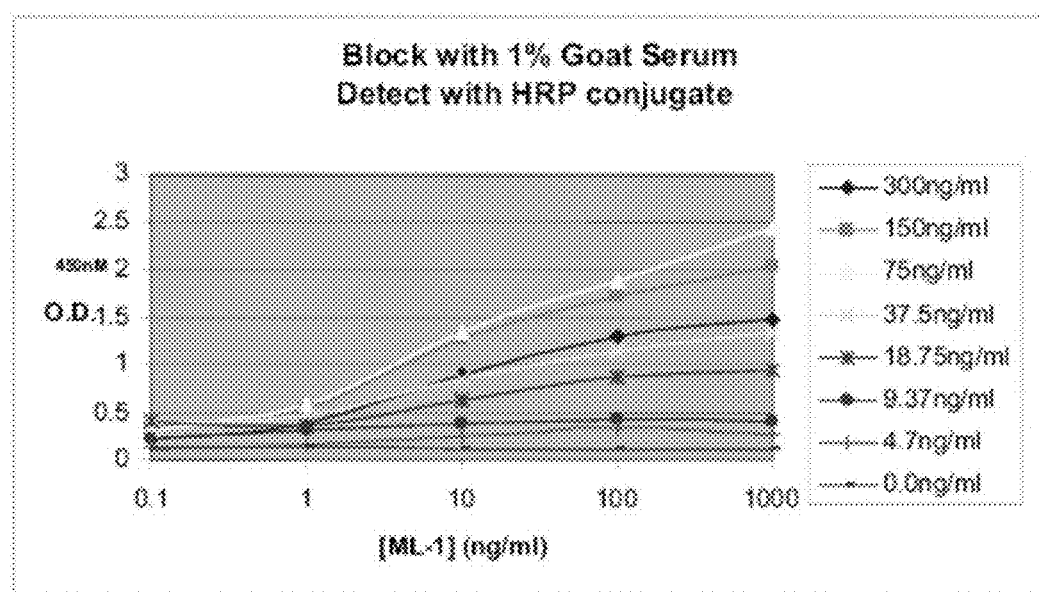
FIGS. 1A and 1B show a FRA-specific binding antibody ML-1 by ELISA and FACS.

The reference works, patents, patent applications, and scientific literature, including accession numbers to Gen- Bank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include Ausubel et al. CURRENT PROTOCOLS IN MOLECULAR BIOLOGY, John Wiley & Sons, New York (1998); Sambrook et al. MOLECULAR CLONING: A LABORATORY MANUAL, 2D ED., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

Each range recited herein includes all combinations and sub-combinations of ranges, as well as specific numerals contained therein.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The invention provides a method for inhibiting the growth of FRA-positive cells, such as but not limited to cancer cells. Such a method may be used to inhibit the progression of neoplastic disease using in-out antibodies that specifically bind to FRA, preferably mammalian FRA, more preferably human FRA (SEQ ID NOs:1 (nucleotide) and 2 (amino acid)). The methods of the invention may be used to modulate the growth of FRA-positive cells, for example, to treat cancer in mammals, including humans. The cancer cells that may be inhibited include all cancer cells that have an increased expression of FRA in relation to normal human tissues, particularly ovarian, breast, colorectal and lung cancer cells.

Without wishing to be bound by any particular theory of operation, it is believed that the increased expression of FRA in cancer cells results in an increased cell surface expression of the membrane bound form on the surface of the cells. Therefore, some cancer cells have an increased expression of FRA relative to normal tissues. Thus, the membrane bound FRA is an ideal target for antibody therapy in cancer.

As used herein, the term "epitope" refers to the portion of an antigen to which an antibody specifically binds.

As used herein, the term "conformational epitope" refers to a discontinuous epitope formed by a spatial relationship between amino acids of an antigen other than an unbroken series of amino acids.

As used herein, the terms "immune effector activity," "immune effector effect," and "immune effector function" refer to the ability of an antibody to kill cells by antibody-dependent cellular cytotoxicity (ADCC) or complement-dependent cytotoxicity (CDC).

As used herein, the term "in-out antibody" refers to an antibody that can internalize within an antigen-presenting cell and, if not internalized, elicits an immune-effector activity.

As used herein, the phrase "in the alternative" when referring to the ability of an antibody to internalize or elicit an immune effector activity means that the antibody has the ability to both internalize and elicit an immune effector activity but cannot do both simultaneously.

As used herein, the term "inhibition of growth of dysplastic cells in vitro" means a decrease in the number of cells, in culture, by about 5%, preferably about 10%, more preferably about 20%, more preferably about 30%, more preferably about 40%, more preferably about 50%, more preferably about 60%, more preferably about 70%, more preferably about 80%, more preferably about 90%, and most preferably about 100%. In vitro inhibition of tumor cell growth may be measured by assays known in the art.

As used herein, the term "inhibition of growth of dysplastic cells in vivo" means a decrease in the number of cells in an organism by about 5%, preferably about 10%, more preferably about 20%, more preferably about 30%, more preferably about 40%, more preferably about 50%, more preferably about 60%, more preferably about 70%, more preferably about 80%, more preferably about 90%, and most preferably about 100%. In vivo modulation of cell growth may be measured by assays known in the art.

As used herein, "dysplastic cells" refer to cells that exhibit abnormal growth. Examples of abnormal growth properties include but are not limited to growth in soft agar, lack of contact inhibition, failure to undergo cell cycle arrest in the absence of serum, and formation of tumors when injected into immuno-compromised mice Dysplastic cells include, but are not limited to tumors, hyperplasia, and the like.

The term "preventing" refers to decreasing the probability that an organism contracts or develops an abnormal condition such as dysplasia.

The term "treating" refers to having a therapeutic effect and at least partially alleviating or abrogating an abnormal condition in the organism. Treating includes maintenance of inhibited tumor growth and induction of remission.

"Therapeutic effect" refers to the reduction, elimination, or prevention of a disease or abnormal condition, symptoms thereof, or side effects thereof in the subject. "Effective amount" refers to an amount necessary to produce a desired effect. A "therapeutically effective amount" means the amount that, when administered to a subject for treating a disease, condition or disorder, is sufficient to effect treatment for that disease. A therapeutic effect relieves to some extent one or more of the symptoms of the abnormal condition. In reference to the treatment of abnormal conditions, a therapeutic effect can refer to one or more of the following: (a) an increase or decrease in the proliferation, growth, and/or differentiation of cells; (b) inhibition (i.e., slowing or stopping) of growth of tumor cells in vivo (c) promotion of cell death; (d) inhibition of degeneration; (e) relieving to some extent one or more of the symptoms associated with the abnormal condition; and (f) enhancing the function of a population of cells. The antibodies and derivatives thereof described herein effectuate the therapeutic effect alone or in combination with conjugates or additional components of the compositions of the invention.

As used herein, the term "inhibits the progression of cancer or neoplastic disease" refers to an activity of a treatment that slows the modulation of neoplastic disease toward end-stage cancer in relation to the modulation toward end-stage disease of untreated cancer cells.

As used herein, the term "neoplastic disease" refers to a condition marked by abnormal proliferation of cells of a tissue.

As used herein the term "biomolecule" refers to any molecule that can be conjugated to, coadministered with, administered before or after administering the antibody, or otherwise used in association with the antibody of the invention. Biomolecules include, but are not limited to, enzymes, proteins, peptides, amino acids, nucleic acids, lipids, carbohydrates, and fragments, homologs, analogs, or derivatives, and combinations thereof. Examples of biomolecules include but are not limited to interleukin-2, interferon alpha, interferon beta, interferon gamma, rituxan, zevalin, herceptin, erbitux, and avastin. The biomolecules can be native, recombinant, or synthesized, and may be modified from their native form with, for example, glycosylations, acetylations, phosphorylations, myristylations, and the like. The term biomolecule as it is used herein is not limited to naturally occurring molecules, and includes synthetic molecules having no biological origin.

As used herein, the term "cytotoxic" or "cytostatic" agent refers to an agent that reduces the viability or proliferative potential of a cell. Cytotoxic or cytostatic agents can function in a variety of ways to reduce cell viability or proliferation, for example, but not by way of limitation, by inducing DNA damage, inducing cell cycle arrest, inhibiting DNA synthesis, inhibiting transcription, inhibiting translation or protein synthesis, inhibiting cell division, or inducing apoptosis. As used herein, the term "chemotherapeutic agent" refers to cytotoxic, cytostatic, and antineoplastic agents that preferentially kill, inhibit the growth of, or inhibit the metastasis of neoplastic cells or disrupt the cell cycle of rapidly proliferating cells. Specific examples of chemotherapeutic agents include, but are not limited to, radionuclides, pokeweed antiviral protein, abrin, ricin and each of their A chains, altretamine, actinomycin D, plicamycin, puromycin, gramicidin D, doxorubicin, colchicine, cytochalasin B, cyclophosphamide, emetine, maytansine, amsacrine, cisplatin, etoposide, etoposide orthoquinone, teniposide, daunorubicin, gemcitabine, doxorubicin, mitoxantraone, bisanthrene, Bleomycin, methotrexate, vindesine, adriamycin, vincristine, vinblastine, BCNU, taxol, tarceva, avastin, mitomycin, modified *Pseudomonas* enterotoxin A, calicheamicin, 5-fluorouracil, cyclophosphamide and certain cytokines such as TNF-alpha and TNF-beta.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

"Recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The phrase "nucleic acid" or "polynucleotide sequence" refers to a single or double-stranded polymer of deoxyribonucleotide or ribonucleotide bases read from the 5' to the 3' end. Nucleic acids can also include modified nucleotides that permit correct read through by a polymerase and do not alter expression of a polypeptide encoded by that nucleic acid, including, for example, conservatively modified variants.

"Polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Polypeptides of the invention, including antibodies of the invention, include conservatively modified variants. One of skill will recognize that substitutions, deletions or additions to a nucleic acid, peptide, polypeptide, or protein sequence which alter, add or delete a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (33). The term "conservative substitution" also includes the use of a substituted amino acid in place of an unsubstituted parent amino acid provided that such a polypeptide also displays the requisite binding activity.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analog" refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones but retain the same basic chemical structure as a naturally occurring amino acid. "Amino acid mimetic" refers to a chemical compound having a structure that is different from the general chemical structure of an amino acid but that functions in a manner similar to a naturally occurring amino acid.

Amino acids can be referred to herein by either their commonly known three letter symbols or by the one-letter symbols recommended by the IUPAC-IUB Biochemical Nomenclature Commission (see Table 1 below). Nucleotides, likewise, can be referred to by their commonly accepted single-letter codes.

TABLE 1

| SYMBOL | | |
| --- | --- | --- |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

It should be noted that all amino acid sequences are represented herein by formulae whose left to right orientation is in the conventional direction of amino-terminus to carboxy-terminus.

As used herein, the term "in vitro" or "ex vivo" refers to an artificial environment and to processes or reactions that occur within an artificial environment, for example, but not limited to, test tubes and cell cultures. The term "in vivo" refers to a natural environment (e.g., an animal or a cell) and to processes or reactions that occur within a natural environment.

"Pharmaceutically acceptable," "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

The term "pharmaceutically acceptable carrier" refers to reagents, excipients, cells, compounds, materials, compositions, and/or dosage forms which are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include gases, liquids, and semi-solid and solid materials.

Except when noted, "subject" or "patient" are used interchangeably and refer to mammals such as human patients and non-human primates, as well as experimental animals such as rabbits, dogs, cats, rats, mice, and other animals. Accordingly, "subject" or "patient" as used herein means any mammalian patient or subject to which the compositions of the invention can be administered. In some embodiments of the present invention, the patient will be suffering from an infectious or inflammatory disease. In some embodiments of the present invention, the patient will have been diagnosed with cancer. In an exemplary embodiment of the present invention, to identify candidate patients for treatment according to the invention, accepted screening methods are employed to determine the status of an existing disease or condition in a subject or risk factors associated with a targeted or suspected disease or condition. These screening methods include, for example, examinations to determine whether a subject is suffering from an infectious disease, an inflammatory disease, or cancer. These and other routine methods allow the clinician to select subjects in need of therapy.

"Therapeutic compound" as used herein refers to a compound useful in the prophylaxis or treatment of a disease or condition such as cancer.

"Concomitant administration," "concurrent administration," or "co-administration" as used herein includes administration of the active agents (e.g., MAbs, chemotherapeutic agents, biomolecules), in conjunction or combination, together, or before or after each other. The multiple agent(s) may be administered by the same or by different routes, simultaneously or sequentially, as long as they are given in a manner sufficient to allow all agents to achieve effective concentrations at the site of action. A person of ordinary skill in the art would have no difficulty determining the appropriate timing, sequence, and dosages of administration for particular drugs and compositions of the present invention.

"Immunoglobulin" or "antibody" is used broadly to refer to both antibody molecules and a variety of antibody-derived molecules and includes any member of a group of glycoproteins occurring in higher mammals that are major components of the immune system. The term "antibody" is used in the broadest sense and specifically covers monoclonal antibodies, antibody compositions with polyepitopic specificity, bispecific antibodies, diabodies, and single-chain molecules, as well as antibody fragments (e.g., Fab, F(ab')$_2$, and F$_v$), so long as they exhibit the desired biological activity. An immunoglobulin molecule includes antigen binding domains, which each include the light chains and the end-terminal portion of the heavy chain, and the Fc region, which is necessary for a variety of functions, such as complement fixation. There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM, respectively. As used herein "immunoglobulin" or "antibody" includes all subclasses of alpha, delta, epsilon, gamma, and mu and also refers to any natural (e.g., IgA and IgM) or synthetic multimers of the four-chain immunoglobulin structure. Antibodies non-covalently, specifically, and reversibly bind an antigen. The term "monoclonal antibody" as used herein refers to an antibody obtained from a population of substantially homogeneous antibodies, i.e., the individual antibodies comprising the population are identical except for possible naturally occurring mutations that can be present in minor amounts. For example, monoclonal antibodies may be produced by a single clone of antibody-producing cells. Unlike polyclonal antibodies, monoclonal antibodies are monospecific (e.g., specific for a single epitope of a single antigen). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention can be made by the hybridoma method first described by Kohler et al., Nature, 256: 495, 1975, or can be made by recombinant DNA methods. The "monoclonal antibodies" can also be isolated from phage antibody libraries using the techniques described in Marks et al., J. Mol. Biol., 222: 581-597, 1991, for example.

Antibody-derived molecules comprise portions of intact antibodies that retain antigen-binding specificity, and comprise, for example, at least one variable region (either a heavy chain or light chain variable region). Antibody-derived molecules, for example, include molecules such as Fab fragments, Fab' fragments, F(ab')$_2$ fragments, Fd fragments, F(v) fragments, Fabc fragments, Fd fragments, Fabc fragments, Sc antibodies (single chain antibodies), diabodies, individual antibody light chains, individual antibody heavy chains, chimeric fusions between antibody chains and other molecules, heavy chain monomers or dimers, light chain monomers or dimers, dimers consisting of one heavy and one light chain, and the like. All classes of immunoglobulins (e.g., IgA, IgD, IgE, IgG and IgM) and subclasses thereof are included.

Antibodies can be labeled or conjugated to toxic or non-toxic moieties. Toxic moieties include, for example, bacterial toxins, viral toxins, radioisotopes, and the like. Antibodies can be labeled for use in biological assays (e.g., radioisotope labels, fluorescent labels) to aid in detection of the antibody. Antibodies can also be labeled/conjugated for diagnostic or therapeutic purposes, e.g., with radioactive isotopes that deliver radiation directly to a desired site for applications such as radioimmunotherapy (Garmestani et al., Nucl. Med. Biol., 28: 409, 2001), imaging techniques and radioimmunoguided surgery or labels that allow for in vivo imaging or detection of specific antibody/antigen complexes. Antibodies may also be conjugated with toxins to provide an immunotoxin (see, Kreitman, R. J. Adv. Drug Del. Rev., 31: 53, 1998).

With respect to antibodies, the term, "immunologically specific" refers to antibodies that bind to one or more epitopes of a protein of interest, but which do not substantially recognize and bind other molecules in a sample containing a mixed population of antigenic biological molecules.

"Chimeric" or "chimerized" antibodies (immunoglobulins) refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al., Proc. Natl. Acad. Sci. U.S.A., 81: 6851-6855, 1984).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Hybridoma" refers to the product of a cell-fusion between a cultured neoplastic lymphocyte and a primed B- or T-lymphocyte which expresses the specific immune potential of the parent cell.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

Various patents and other publications are cited herein and throughout the specification, each of which is incorporated by reference herein in its entirety.

Antibodies

The antibodies of the invention specifically bind FRA and exhibit in-out activity (i.e., in the alternative, the ability to induce an immune effector activity and the ability to internalize in FRA-positive cells). In some embodiments, the antibodies bind to the same epitope as LK26 or MOv18. In other embodiments, the antibodies bind to an epitope other than that bound by LK26 or MOv18. FRA to which the antibodies of the invention bind is preferably mammalian, more preferably human. Human FRA is encoded by SEQ ID NO:1 and comprises an amino acid sequence of SEQ ID NO:2:

SEQ ID NO 1: cDNA of Human Mature Folate Receptor Alpha

```
  1 attgcatggg ccaggactga gcttctcaat gtctgcatga acgccaagca ccacaaggaa 61 aagccaggcc ccgaggacaa gttgcatgag cagtgtcgac cctggaggaa gaatgcctgc 121 tgttctacca acaccagcca ggaagcccat aaggatgttt cctacctata tagattcaac 181 tggaaccact gtggagagat ggcacctgcc tgcaaacggc atttcatcca ggacacctgc 241 ctctacgagt gctcccccaa cttggggccc tggatccagc aggtggatca gagctggcgc 301 aaagagcggg tactgaacgt gcccctgtgc aaagaggact gtgagcaatg gtgggaagat 361 tgtcgcacct cctacacctg caagagcaac tggcacaagg gctggaactg gacttcaggg 421 tttaacaagt gcgcagtggg agctgcctgc caaccttttcc atttctactt ccccacaccc 481 actgttctgt gcaatgaaat ctggactcac tcctacaagg tcagcaacta cagccgaggg 541 agtggccgct gcatccagat gtggttcgac ccagcccagg gcaacccccaa tgaggaggtg 601 gcgaggttct atgctgcagc catgagtggg gctgggccct gggcagcctg gcctttcctg 661 cttagcctgg ccctaatgct gctgtggctg ctcagc
```

SEQ ID NO 2: Polypeptide Sequence of Human Mature Folate Receptor Alpha

```
  1 iawartelln vcmnakhhke kpgpedklhe qcrpwrknac cstntsqeah kdvsylyrfn 61 wnhcgemapa ckrhfiqdtc lyecspnlgp wiqqvdqswr kervlnvplc kedceqwwed 121 crtsytcksn whkgwnwtsg fnkcavgaac qpfhfyfptp tvlcneiwth sykvsnysrg 181 sgrciqmwfd paqgnpneev arfyaaamsg agpwaawpfl lslalmllwl ls
```

Preferred antibodies, and antibodies suitable for use in the methods of the invention, include, for example, fully human antibodies, human antibody homologs, single chain antibodies, humanized antibody homologs, chimeric antibodies, chimeric antibody homologs, and monomers or dimers of antibody heavy or light chains or mixtures thereof.

The antibodies of the invention may include intact immunoglobulins of any isotype including types IgA, IgG, IgE, IgD, IgM (as well as subtypes thereof). The light chains of the immunoglobulin may be kappa or lambda.

The antibodies of the invention include portions of intact antibodies that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. Thus, antigen-binding fragments, as well as full-length dimeric or trimeric polypeptides derived from the above-described antibodies are themselves useful for exhibiting in-out activity.

It was found that the direct use of rodent monoclonal antibodies as human therapeutic agents led to human anti-rodent antibody ("HARA") responses which occurred in a significant number of patients treated with the rodent-derived antibody (Khazaeli, et al. (1994) *Immunother.* 15:42-52). Chimeric antibodies containing less rodent amino acid sequence were thought to circumvent the problem of eliciting an immune response in humans.

Chimeric antibodies may be produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody. One approach, described in EP 0239400 to Winter et al. describes the substitution of one species' complementarity determining regions (CDRs) for those of another species, such as substituting the CDRs from human heavy and light chain immunoglobulin variable region domains with CDRs from mouse variable region domains. These altered antibodies may subsequently be combined with human immunoglobulin constant regions to form antibodies that are human except for the substituted murine CDRs which are specific for the antigen. Methods for grafting CDR regions of antibodies may be found, for example in Riechmann et al. (1988) *Nature* 332:323-327 and Verhoeyen et al. (1988) *Science* 239:1534-1536.

As a non-limiting example, a method of performing CDR grafting may be performed by sequencing the mouse heavy and light chains of the antibody of interest that binds to the target antigen (e.g., FRA) and genetically engineering the CDR DNA sequences and imposing these amino acid sequences to corresponding human V regions by site-directed mutagenesis. Human constant region gene segments of the desired isotype are added, and the chimeric heavy and light chain genes are co-expressed in mammalian cells to produce soluble antibody. A typical expression cell is a Chinese Hamster Ovary (CHO) cell. Other expression cells include HEK293 and myeloma cells. Suitable methods for creating the chimeric antibodies may be found, for example, in Jones et al. (1986) *Nature* 321:522-525; Riechmann (1988) *Nature* 332:323-327; Queen et al. (1989) *Proc. Nat. Acad. Sci. USA* 86:10029; and Orlandi et al. (1989) *Proc. Natl. Acad. Sci. USA* 86:3833.

Further refinement of antibodies to avoid the problem of HARA responses led to the development of "humanized antibodies." Humanized antibodies are produced by recombinant DNA technology, in which at least one of the amino acids of a human immunoglobulin light or heavy chain that is not required for antigen binding has been substituted for the corresponding amino acid from a nonhuman mammalian immunoglobulin light or heavy chain. For example, if the immunoglobulin is a mouse monoclonal antibody, at least one amino acid that is not required for antigen binding is substituted using the amino acid that is present on a corresponding human antibody in that position. Without wishing to be bound by any particular theory of operation, it is believed that the "humanization" of the monoclonal antibody inhibits human immunological reactivity against the foreign immunoglobulin molecule.

Queen et al. (1989) *Proc. Nat. Acad. Sci. USA* 86:10029-10033 and WO 90/07861 describe the preparation of a humanized antibody. Human and mouse variable framework regions were chosen for optimal protein sequence homology. The tertiary structure of the murine variable region was computer-modeled and superimposed on the homologous human framework to show optimal interaction of amino acid residues with the mouse CDRs. This led to the development of antibodies with improved binding affinity for antigen (which is typically decreased upon making CDR-grafted chimeric antibodies). Alternative approaches to making humanized antibodies are known in the art and are described, for example, in Tempest (1991) *Biotechnology* 9:266-271.

The antibodies of the invention include derivatives that are modified, e.g., by the covalent attachment of any type of molecule to the antibody such that covalent attachment does not prevent the antibody from binding to its epitope. Examples of suitable derivatives include, but are not limited to glycosylated antibodies and fragments, acetylated antibodies and fragments, pegylated antibodies and fragments, phosphorylated antibodies and fragments, and amidated antibodies and fragments. The antibodies and derivatives thereof of the invention may themselves be derivatized by known protecting/blocking groups, proteolytic cleavage, linkage to a cellular ligand or other proteins, and the like. Further, the antibodies and derivatives thereof of the invention may contain one or more non-classical amino acids.

The antibodies of the invention include variants having single or multiple amino acid substitutions, deletions, additions, or replacements that retain the biological properties (e.g., internalization, binding affinity or avidity, or immune effector activity) of the antibodies of the invention. The skilled person can produce variants having single or multiple amino acid substitutions, deletions, additions or replacements. These variants may include, inter alia: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In another embodiment, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art. Antibodies of the invention also include antibody fragments. A "fragment" refers to polypeptide sequences which are preferably at least about 40, more preferably at least to about 50, more preferably at least about 60, more preferably at least about 70, more preferably at least about 80, more preferably at least about 90, and more preferably at least about 100 amino acids in length, and which retain some biological activity or immunological activity of the full-length sequence, for example, FRA binding affinity or avidity, the ability to internalize, and immune effector activity.

The invention also encompasses fully human antibodies such as those derived from peripheral blood mononuclear cells of FRA-linked cancer patients. Such cells may be fused with myeloma cells, for example to form hybridoma cells producing fully human antibodies against FRA.

The antibodies and derivatives thereof of the invention have binding affinities that include a dissociation constant ($K_d$) of less than $1\times10^{-2}$. In some embodiments, the $K_d$ is less than $1\times10^{-3}$. In other embodiments, the $K_d$ is less than $1\times10^{-4}$. In some embodiments, the $K_d$ is less than $1\times10^{-5}$. In still other embodiments, the $K_d$ is less than $1\times10^{-6}$. In other embodiments, the $K_d$ is less than $1\times10^{-7}$. In other embodiments, the $K_d$ is less than $1\times10^{-8}$. In other embodiments, the $K_d$ is less than $1\times10^{-9}$. In other embodiments, the $K_d$ is less than $1\times10^{-10}$. In still other embodiments, the $K_d$ is less than $1\times10^{-11}$. In some embodiments, the $K_d$ is less than $1\times10^{-12}$. In other embodiments, the $K_d$ is less than $1\times10^{-13}$. In other embodiments, the $K_d$ is less than $1\times10^{-14}$. In still other embodiments, the $K_d$ is less than $1\times10^{-15}$.

Without wishing to be bound by any particular theory of operation, it is believed that the antibodies of the invention are particularly useful to bind FRA due to an increased avidity of the antibody as both "arms" of the antibody ($F_{ab}$ fragments) bind to separate FRA molecules. This leads to a decrease in the dissociation ($K_d$) of the antibody and an overall increase in the observed affinity ($K_D$). In addition, antibodies of this invention must bind to epitopes that allow for the internalization of the antibody-antigen complex. These are especially good features for targeting tumors as the antibodies of the invention will bind more tightly to tumor tissue than normal tissue to attract immune cells for cytotoxicity and be capable of internalizing for delivery of conjugated agents for added therapeutic effects.

The antibodies of the invention may be used alone or with one or more biomolecules or chemotherapeutic agents such as a cytotoxic or cytostatic agent. In some embodiments, the chemotherapeutic agent is a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the chemotherapeutic agent is a toxin or cytotoxic drug, including but not limited to ricin, modified *Pseudomonas* enterotoxin A, calicheamicin, adriamycin, 5-fluorouracil, and the like. Methods of conjugation of antibodies and antibody fragments to such agents are known in the literature.

Also included in the invention are cells producing the in-out antibodies of the invention. The antibody-producing cells of the invention may be bacterial, yeast, insect, and animal cells, preferably, mammalian cells. For example, the antibody-producing cells of the invention include insect cells, such as for example, *Spodoptera frugiperda* cells; yeast cells, such as, for example, *Saccharomyces cerevisiae* and *Schizosaccharomyces pombe* cells; and mammalian cells such as, for example Chinese Hamster Ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK cells, mouse sertoli cells, human cervical carcinoma cells, buffalo rat liver cells, human lung cells, human liver cells, mouse mammary tumor cells, TRI cells, MRC 5 cells, and FS4 cells. Antibody-producing cells have been placed with the Amer. Type Cult. Coll. (10801 University Blvd., Manassas, Va. 20110-2209) on Apr. 24, 2006 and have been assigned Access. No. PTA-7552. Examples of in-out antibodies of the invention are antibodies produced by such cells.

Nucleic Acids

The invention also includes nucleic acids encoding the heavy chain and/or light chain of the anti-FRA antibodies of the invention. "Nucleic acid" or a "nucleic acid molecule" as used herein refers to any DNA or RNA molecule, either single- or double-stranded and, if single-stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. In some embodiments of the invention, nucleic acids are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

Nucleic acids of the invention include nucleic acids having at least 80%, more preferably at least about 90%, more preferably at least about 95%, and most preferably at least about 98% homology to nucleic acids of the invention. The terms "percent similarity", "percent identity" and "percent homology" when referring to a particular sequence are used as set forth in the University of Wisconsin GCG software program. Nucleic acids of the invention also include complementary nucleic acids. In some instances, the sequences will be fully complementary (no mismatches) when aligned. In other instances, there may be up to about a 20% mismatch in the sequences.

Nucleic acids of the invention also include fragments of the nucleic acids of the invention. A "fragment" refers to a nucleic acid sequence that is preferably at least about 10 nucleic acids in length, more preferably about 40 nucleic acids, and most preferably about 100 nucleic acids in length. A "fragment" can also mean a stretch of at least about 100 consecutive nucleotides that contains one or more deletions, insertions, or substitutions. A "fragment" can also mean the whole coding sequence of a gene and may include 5' and 3' untranslated regions.

Nucleic acids of the invention can be cloned into a vector. A "vector" is a replicon, such as a plasmid, cosmid, bacmid, phage, artificial chromosome (BAC, YAC) or virus, into which another genetic sequence or element (either DNA or RNA) may be inserted so as to bring about the replication of the attached sequence or element. A "replicon" is any genetic element, for example, a plasmid, cosmid, bacmid, phage, artificial chromosome (BAC, YAC) or virus, that is capable of replication largely under its own control. A replicon may be either RNA or DNA and may be single- or double-stranded. In some embodiments, the expression vector contains a constitutively active promoter segment (such as but not limited to CMV, SV40, Elongation Factor or LTR sequences) or an inducible promoter sequence such as the steroid inducible pIND vector (Invitrogen), where the expression of the nucleic acid can be regulated. Expression vectors of the invention may further comprise regulatory sequences, for example, an internal ribosomal entry site. The expression vector can be introduced into a cell by transfection, for example.

Nucleic acids encoding antibodies of the invention may be recombinantly expressed. The expression cells of the invention include any insect expression cell line known, such as for example, *Spodoptera frugiperda* cells. The expression cell lines may also be yeast cell lines, such as, for example, *Saccharomyces cerevisiae* and *Schizosaccharomyces pombe* cells. The expression cells may also be mammalian cells such as, for example Chinese Hamster Ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK cells, mouse sertoli cells, human cervical carcinoma cells, buffalo rat liver cells, human lung cells, human liver cells, mouse mammary tumor cells, TRI cells, MRC 5 cells, and FS4 cells. Nucleic acids of the invention may be introduced into a cell by transfection, for example. Recombinantly expressed antibodies may be recovered from the growth medium of the cells, for example.

Methods of Producing in-Out Antibodies to FRA

Immunizing Animals

The invention also provides methods of producing in-out monoclonal antibodies that specifically bind to FRA. FRA may be purified from cells or from recombinant systems using a variety of well-known techniques for isolating and purifying proteins. For example, but not by way of limitation, FRA may be isolated based on the apparent molecular weight of the protein by running the protein on an SDS-PAGE gel and blotting the proteins onto a membrane. Thereafter, the appropriate size band corresponding to FRA may be cut from the membrane and used as an immunogen in animals directly, or by first extracting or eluting the protein from the membrane. As an alternative example, the protein may be isolated by size-exclusion chromatography alone or in combination with other means of isolation and purification. Other means of purification are available in such standard reference texts as Zola, MONOCLONAL ANTIBODIES: PREPARATION AND USE OF MONOCLONAL ANTIBODIES AND ENGINEERED ANTIBODY DERIVATIVES (BASICS: FROM BACKGROUND TO BENCH) Springer-Verlag Ltd., New York, 2000; BASIC METHODS IN ANTIBODY PRODUCTION AND CHARACTERIZATION, Chapter 11, "Antibody Purification Methods," Howard and Bethell, Eds., CRC Press, 2000; ANTIBODY ENGINEERING (SPRINGER LAB MANUAL.), Kontermann and Dubel, Eds., Springer-Verlag, 2001.

One strategy for generating in-out antibodies against FRA involves immunizing animals with cells expressing FRA. Animals so immunized will produce antibodies against the protein. Standard methods are known for creating monoclonal antibodies including, but are not limited to, the hybridoma technique (see Kohler & Milstein, (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

Antibodies of the invention may be produced in vivo or in vitro. For in vivo antibody production, animals are generally immunized with an immunogenic portion of FRA. The antigen or antigen-positive cell is generally combined with an adjuvant to promote immunogenicity. Adjuvants vary according to the species used for immunization. Examples of adjuvants include, but are not limited to: Freund's complete adjuvant ("FCA"), Freund's incomplete adjuvant ("FIA"), mineral gels (e.g., aluminum hydroxide), surface active substances (e.g., lysolecithin, pluronic polyols, polyanions), peptides, oil emulsions, keyhole limpet hemocyanin ("KLH"), dinitrophenol ("DNP"), and potentially useful human adjuvants such as Bacille Calmette-Guerin ("BCG") and *corynebacterium parvum*. Such adjuvants are also well known in the art.

Immunization may be accomplished using well-known procedures. The dose and immunization regimen will depend on the species of mammal immunized, its immune status, body weight, and/or calculated surface area, etc. Typically, blood serum is sampled from the immunized mammals and assayed for anti-FRA antibodies using appropriate screening assays as described below, for example.

Splenocytes from immunized animals may be immortalized by fusing the splenocytes (containing the antibody-producing B cells) with an immortal cell line such as a myeloma line. Typically, myeloma cell line is from the same species as the splenocyte donor. In one embodiment, the immortal cell line is sensitive to culture medium containing hypoxanthine, aminopterin and thymidine ("HAT medium"). In some embodiments, the myeloma cells are negative for Epstein-Barr virus (EBV) infection. In preferred embodiments, the myeloma cells are HAT-sensitive, EBV negative and Ig expression negative. Any suitable myeloma may be used. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC. These myeloma cells are fused to the donor splenocytes polyethylene glycol ("PEG"), preferably 1500 molecular weight polyethylene glycol ("PEG 1500"). Hybridoma cells resulting from the fusion are selected in HAT medium which kills unfused and unproductively fused myeloma cells. Unfused splenocytes die over a short period of time in culture. In some embodiments, the myeloma cells do not express immunoglobulin genes.

Hybridomas producing a desired antibody which are detected by screening assays such as those described below, may be used to produce antibodies in culture or in animals. For example, the hybridoma cells may be cultured in a nutrient medium under conditions and for a time sufficient to allow the hybridoma cells to secrete the monoclonal antibodies into the culture medium. These techniques and culture media are well known by those skilled in the art. Alternatively, the hybridoma cells may be injected into the peritoneum of an unimmunized animal. The cells proliferate in the peritoneal cavity and secrete the antibody, which accumulates as ascites fluid. The ascites fluid may be withdrawn from the peritoneal cavity with a syringe as a rich source of the monoclonal antibody.

Another non-limiting method for producing human antibodies is described in U.S. Pat. No. 5,789,650 which describes transgenic mammals that produce antibodies of another species (e.g., humans) with their own endogenous immunoglobulin genes being inactivated. The genes for the heterologous antibodies are encoded by human immunoglobulin genes. The transgenes containing the unrearranged immunoglobulin encoding regions are introduced into a non-human animal. The resulting transgenic animals are capable of functionally rearranging the transgenic immunoglobulin sequences and producing a repertoire of antibodies of various isotypes encoded by human immunoglobulin genes. The B-cells from the transgenic animals are subsequently immortalized by any of a variety of methods, including fusion with an immortalizing cell line (e.g., a myeloma cell).

In-out antibodies against FRA may also be prepared in vitro using a variety of techniques known in the art. For example, but not by way of limitation, fully human monoclonal antibodies against FRA may be prepared by using in vitro-primed human splenocytes (Boerner et al. (1991) *J. Immunol.* 147:86-95).

Alternatively, for example, the antibodies of the invention may be prepared by "repertoire cloning" (Persson et al. (1991) *Proc. Nat. Acad. Sci. USA* 88:2432-2436; and Huang and Stollar (1991) *J. Immunol. Methods* 141:227-236). Further, U.S. Pat. No. 5,798,230 describes preparation of human monoclonal antibodies from human B antibody-producing B cells that are immortalized by infection with an Epstein-Barr virus that expresses Epstein-Barr virus nuclear antigen 2 (EBNA2). EBNA2, required for immortalization, is then inactivated resulting in increased antibody titers.

In another embodiment, in-out antibodies against FRA are formed by in vitro immunization of peripheral blood mononuclear cells ("PBMCs"). This may be accomplished by any means known in the art, such as, for example, using methods described in the literature (Zafiropoulos et al. (1997) *J. Immunological Methods* 200:181-190).

Another strategy for generating in-out antibodies against FRA involves immunizing animals with peptides corresponding to regions of the membrane bound form of FRA that allow for internalization of antibodies that retain robust immune effector activity. Animals so immunized will produce antibodies against the protein. Standard methods are known for creating monoclonal antibodies including, but are not limited to, the hybridoma technique (see Kohler & Milstein, (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

In one embodiment of the invention, the procedure for in vitro immunization is supplemented with directed evolution of the hybridoma cells in which a dominant negative allele of a mismatch repair gene such as PMS1, PMS2, PMS2-134, PMSR2, PMSR3, MLH1, MLH2, MLH3, MLH4, MLH5, MLH6, PMSL9, MSH1, and MSH2 is introduced into the hybridoma cells after fusion of the splenocytes, or to the myeloma cells before fusion. Cells containing the dominant negative mutant will become hypermutable and accumulate mutations at a higher rate than untransfected control cells. A pool of the mutating cells may be screened for clones that produce higher affinity antibodies, or that produce higher titers of antibodies, or that simply grow faster or better under certain conditions. The technique for generating hypermutable cells using dominant negative alleles of mismatch repair genes is described in U.S. Pat. No. 6,146,894, issued Nov. 14, 2000. Alternatively, mismatch repair may be inhibited using the chemical inhibitors of mismatch repair described by Nicolaides et al. in WO 02/054856 "Chemical Inhibitors of Mismatch Repair" published Jul. 18, 2002. The technique for enhancing antibodies using the dominant negative alleles of mismatch repair genes or chemical inhibitors of mismatch repair may be applied to mammalian expression cells expressing cloned immunoglobulin genes as well. Cells expressing the dominant negative alleles can be "cured" in that the dominant negative allele can be turned off, if inducible, eliminated from the cell and the like such that the cells become genetically stable once more and no longer accumulate mutations at the abnormally high rate.

Screening for in-Out Antibodies

Screening for in-out antibodies that specifically bind to FRA may be accomplished using an enzyme-linked immunosorbent assay (ELISA), by screening antibodies for immune effector activity, and/or by assaying for internalization. Antibodies exhibiting immune effector activity may be identified using a standard immune effector assay to monitor antibody-dependent cellular cytotoxicity (ADCC) or complement-dependent cytotoxicity (CDC). Antibodies that can be internalized can be identified by conjugating the antibody with a detectable label, such as a fluorochrome or prodrug, to monitor ability to internalize by visualization or toxicity. One or more of these assays (ELISA, immune effector assay, and internalization assay) may be performed in any order to identify in-out antibodies of the invention.

For example, the ELISA may comprise coating microtiter plates with immunizing antigen (whole protein or peptides). Antibodies from positively reacting clones can be screened for reactivity in an ELISA-based assay to FRA. Antibodies specific to the alpha form of folate receptor can be identified by ELISA employing one or more other isotypes of folate receptor. Clones that produce antibodies that are reactive to FRA are selected for further expansion and development. Confirmation of FRA-reactive antibodies exhibiting in-out activity may be accomplished, for example, using a standard immune effector assay to monitor antibody-dependent cellular cytotoxicity (ADCC) or complement-dependent cytotoxicity (CDC). FRA-specific antibodies exhibiting immune effector activity can then be conjugated with a fluorochrome or prodrug to monitor ability to internalize by visualization or toxicity that occurs when prodrug is internalized and liberated from the antibody leading to the presence of the toxin.

Pharmaceutical Compositions of Antibodies

Another aspect of the invention features a pharmaceutical composition of anti-FRA antibodies of the invention. The pharmaceutical compositions may be used to inhibit or reduce growth of FRA-positive cells in a patient. In certain embodiments, the pharmaceutical composition is formulated for administration by injection or infusion.

Pharmaceutical compositions of the invention may further comprise one or more biomolecule, chemotherapeutic agent, or antifolate compound. Examples of antifolate compounds include but are not limited to 5-fluoro-2'-deoxy-uridine-5'-monophosphate (FdUMP), 5-fluorouracil, leucovorin, ZD1649, MTA, GW1843U89, ZD9331, AG337, and PT523. In some embodiments, the antibody is conjugated to the biomolecule, antifolate compound, or chemotherapeutic agent. Suitable chemotherapeutic agents include but are not limited to a radioisotope, including, but not limited to Lead-212, Bismuth-212, Astatine-211, Iodine-131, Scandium-47, Rhenium-186, Rhenium-188, Yttrium-90, Iodine-123, Iodine-125, Bromine-77, Indium-111, and fissionable nuclides such as Boron-10 or an Actinide. In other embodiments, the agent is a toxin or cytotoxic drug, including but not limited to ricin, modified *Pseudomonas* enterotoxin A, calicheamicin, adriamycin, 5-fluorouracil, and the like.

Pharmaceutical compositions of the invention may be formulated with a pharmaceutically acceptable carrier or medium. Suitable pharmaceutically acceptable carriers include water, PBS, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations can be sterilized, and if desired, mixed with auxiliary agents such as lubricants, preservatives, stabilizers, wetting agents, emulsifiers, salts for influencing osmotic pressure, buffers, and coloring. Pharmaceutical carriers suitable for use in the present invention are known in the art and are described, for example, in Pharmaceutical Sciences ($17^{th}$ Ed., Mack Pub. Co., Easton, Pa.).

Kits

According to yet another aspect of the invention, a kit is provided for inhibiting or reducing growth of FRA-positive cells in vitro or in vivo. Also provided are kits for identifying the presence of FRA-positive cells in vitro or in vivo.

The kits of the invention comprise antibody or an antibody composition of the invention and instructions for using the kit in a method for inhibiting or reducing growth of FRA-positive cells, preferably dysplastic cells, in vitro or in vivo or in a method for identifying the presence of FRA-positive cells, preferably dysplastic cells, in a biological sample. The kit may comprise at least one biomolecule, antifolate compound, or chemotherapeutic agent. The kit may comprise at least one diagnostic reagent. An example of a diagnostic reagent is a detectable label, for example but not limited to a radioactive, fluorescent, or chromophoric agent (e.g., $^{111}$In-DOTA). The detectable label may comprise an enzyme. The kit may comprise instructions and/or means for administering the antibody or antibody composition, for example, by injection or infusion.

Methods of Detecting a FRA-Positive Cell

The methods of the invention include methods of detecting cells, such as dysplastic cells, presenting FRA on the surface, including but not limited to ovarian, pancreatic, prostate, or lung cancer cells. The method may be performed in vitro on a biological sample or in vivo. Methods of detecting FRA-positive cells according to the invention comprise contacting anti-FRA antibody of the invention with a biological sample or administering anti-FRA antibody of the invention to a patient, wherein the antibody is labeled with a detectable label, for example but not limited to a radioactive, fluorescent, or chromophoric agent (e.g., $^{111}$In-DOTA), and determining binding of the antibody to cells. The detectable label may be an enzyme.

Methods of Reducing the Growth of FRA-Positive Cells

The in-out anti-FRA antibodies of the invention are suitable for use in reducing the growth of FRA-positive cells in vitro or in vivo. The methods of the invention are suitable for use in humans and non-human animals identified as having a neoplastic condition associated with an increased expression of FRA. Non-human animals which benefit from the invention include pets, exotic (e.g., zoo animals) and domestic livestock. Preferably the non-human animals are mammals.

The invention is suitable for use in a human or animal patient that is identified as having a dysplastic disorder that is marked by increased expression of FRA in the neoplasm in relation to normal tissues. Once such a patient is identified as in need of treatment for such a condition, the method of the invention may be applied to effect treatment of the condition. Dysplastic tissues that may be treated include, but are not limited to ovary, lung, pancreas, and prostate.

The antibodies and derivatives thereof for use in the invention may be administered orally in any acceptable dosage form such as capsules, tablets, aqueous suspensions, solutions or the like. The antibodies and derivatives thereof may also be administered parenterally. That is via the following routes of administration: subcutaneous, intravenous, intramuscular, intra-articular, intra-synovial, intrasternal, intranasal, topically, intrathecal, intrahepatic, intralesional, and intracranial injection or infusion techniques. Generally, the antibodies and derivatives will be provided as an intramuscular or intravenous injection.

The antibodies and derivatives of the invention may be administered alone or with a pharmaceutically acceptable carrier, including acceptable adjuvants, vehicles and excipients.

The antibodies and derivatives of the invention may also be administered with one or more antifolate compounds. The antifolate compounds include, but are not limited to 5-fluoro-2'-deoxy-uridine-5'-monophosphate (FdUMP); 5-fluorouracil (5-FU); L-5-formyltetrahydrofolate ("leucovorin"); N-[5-(N-(3,4-dihydro-2-methyl-4-oxoquinazolin-6-yl-methyl)-amino)-2-thenyl)]-L-glutamic acid ("ZD1649"; also known as "Tomudex") (Jackman et al. (1991) Cancer Res. 51:5579-5586); N-(4-(2-(2-amino-4,7-dihydro-4-oxo-3H-pyrrolo[2,3-D]pyrimidin-5-yl)-ethyl)-benzoyl]-L-glutamic acid ("multi-targeted antifolate" (MTA) also known as "LY231514," "ALIMTA," and "Pemetrexed")(Taylor et al. (1992) J. Med. Chem. 35:4450-4454; Shih et al. (1997) Cancer Res. 57:1116-1123); (S)-2-(5)-(((1,2-dihydro-3-methyl-1-oxobenzo(f)quinazolin-9-yl)-methyl)-amino)-oxo-2-isoindolinyl)-glutaric acid ("GW1843U89") (Hanlon and Ferone (1996) Cancer Res. 56:3301-3306); (2S)-2-{O-fluoro-p-[N-(2,7-dimethyl-4-oxo-3,4-dihydro-quinazolin-6-yl-methyl)-N-prop-2-ynyl)amino]benzamido}-4-(tetrazol-5-yl)-butyric acid ("ZD9331") (Jackman et al. (1997) Clin. Cancer Res. 3:911-921); 3,4-dihydro-amino-6-methyl-4-oxo-5-(4-pyridylthio)-quinazoline ("AG337" also known as "Thymitaq") (Webber et al. (1996) Cancer Chemother. Pharmacol. 37:509-517; Rafi et al. (1998) J. Clin. Oncol. 16:1331-1341), and Nα-(4-amino-4-deoxypteroyl)-N$^δ$-(hemiphthaloyl-L-ornithine) ("PT523") (Rhee et al. (1994) Mol. Pharmacol. 45:783-791; Rowowsky (1999) Curr. Med. Chem. 6:329-352). The antifolate compounds may be administered before, after, or simultaneously with the anti-FR-α antibodies of the invention. The amounts of antifolate compounds to be administered may be the dosages currently used, or may be increased or decreased, as can readily be determined by a physician based on achieving decreased tumor growth or tumor elimination without causing any untoward effects on the patient.

The antibodies of the invention may be administered before, after, or simultaneously with another therapeutic or diagnostic agent. For example, the in-out antibodies of the invention may be administered alone or with a cytotoxic agent such as but not limited to adriamycin, doxorubicin, gemcitabine, or 5-fluorouracil. The in-out antibodies of the invention may be administered alone or with a cytostatic agent such as but not limited to tarceva and avastin. The in-out antibodies and derivatives of the invention may be administered alone or with a vaccine agent. The in-out antibodies and derivatives of the invention may be administered alone or with another biomolecule such as but not limited to interleukin-2, interferon alpha, interferon beta, interferon gamma, rituxan, zevalin, herceptin, erbitux, avastin.

The in-out antibodies and derivatives of the invention may be administered as a homogeneous mixture of unconjugated or conjugated antibody or as a heterogeneous mixture of unconjugated and conjugated in-out antibody.

The effective dosage will depend on a variety of factors and it is well within the purview of a skilled physician to adjust the dosage for a given patient according to various parameters such as body weight, the goal of treatment, the highest tolerated dose, the specific formulation used, the route of administration and the like. Generally, dosage levels of between about 0.001 and about 100 mg/kg body weight per day of the antibody or derivative thereof are suitable. In some embodiments, the dose will be about 0.1 to about 50 mg/kg body weight per day of the antibody or derivative thereof. In other embodiments, the dose will be about 0.1 mg/kg body weight/day to about 20 mg/kg body weight/day. In still other embodiments, the dose will be about 0.1 mg/kg body weight/day to about 10 mg/kg body weight/day. Dosing may be as a bolus or an infusion. Dosages may be given once a day or multiple times in a day. Further, dosages may be given multiple times of a period of time. In some embodiments, the doses are given every 1-14 days. In some embodiments, the antibodies or derivatives thereof are given as a dose of about. 3 to 1 mg/kg i.p. In other embodiments, the antibodies of derivatives thereof are provided at about 5 to 12.5 mg/kg i.v. In still other embodiments, the antibodies or derivatives thereof are provided such that a plasma level of at least about 1 ug/ml is maintained.

Effective treatment may be assessed in a variety of ways. In one embodiment, effective treatment is determined by a slowed progression of tumor growth. In other embodiments, effective treatment is marked by shrinkage of the tumor (i.e., decrease in the size of the tumor). In other embodiments, effective treatment is marked by inhibition of metastasis of the tumor. In still other embodiments, effective therapy is measured by increased well-being of the patient including such signs as weight gain, regained strength, decreased pain, thriving, and subjective indications from the patient of better health.

The following Examples are provided to illustrate the present invention, and should not be construed as limiting thereof.

EXAMPLES

Example 1

In-Out Antibodies that can Bind to FRA

The monoclonal antibody ML-1 was developed by grafting the CDRs of the variable domain of a murine antibody specific to FRA onto a human IgG1 constant region. The antibody was shown to bind specifically to FRA protein and cancer cells expressing FRA and was found to have a binding constant of about 5 nM using Biacore®. To demonstrate FRA-specific binding, antigen-specific ELISA were performed using recombinant FRA in a 96-well format following methods used by those skilled in the art (FIG. 1A).

Figure 1B:
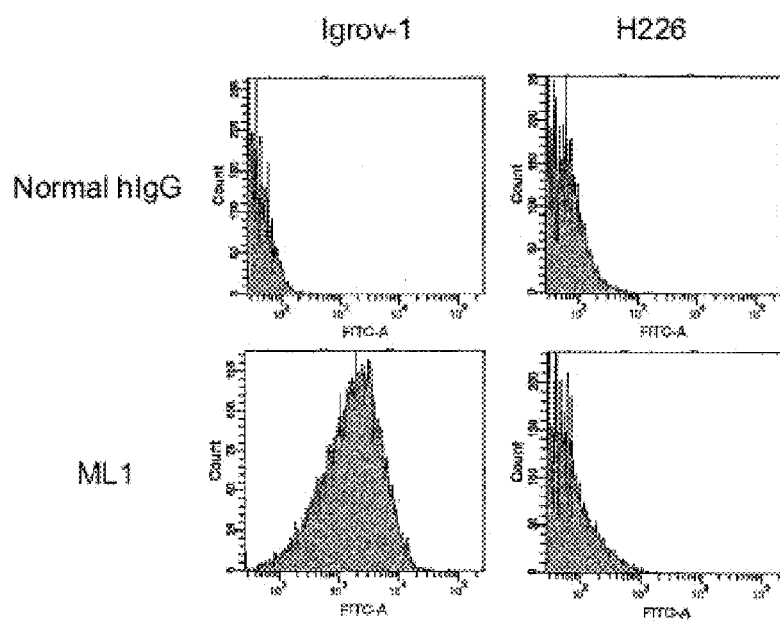

Antibodies found to react by ELISA were further analyzed for FRA binding using FACS analysis following the manufacturer's protocol. Shown in FIG. 1B are representative data of the FACS analysis whereby FRA-expressing ovarian tumor cells were positive for ML-1 binding in contrast to null cells. Antigen-specific ELISA can be also formatted using whole cells expressing FRA, membrane preparations obtained from such FRA expressing cells, or synthetic, overlapping peptides encompassing the entire FRA amino acid sequence.

Example 2

Activity of ML-1 antibody for immune effector activity was assessed by standard antibody-dependent cellular cytotoxicity (ADCC) assays on the FRA-expressing OVCAR-3 cell line. Briefly, OVCAR-3 target cells are seeded in flat-bottom 96-well microplates in complete growth medium (RPMI-1640 containing 10% FBS, 2 mM L-glutamine). The following day, the complete medium is replaced with 100 ul of CHO-CD serum-free medium (Sigma) and 50 ul of antibody-containing conditioned medium is added to target cells and incubated for 20 minutes at 37° C. Subsequently, 100 ul of serum-free medium containing $2 \times 10^5$ effector cells are added to each well and cells are incubated for 5-6 hours at 37° C., 5% $CO_2$. Effector cells are derived from human peripheral blood mononuclear cells (PBMCs), isolated from healthy donors (purchased from Interstate Blood Bank). Prior to use in ADCC, PBMCs are activated by seeding PBMCs at $2.5 \times 10^6$/ml in complete RPMI containing about 10 ng/ml human recombinant interleukin 2 (R&D Systems) for 3 days at 37° C., 5% $CO_2$. Activated PBMCs are then added to OVCAR-3 cells at an effector:target cell ratio of 5:1 and cultures are incubated for 5-6 hours at 37° C., 5% $CO_2$. Supernatant is then collected from each well and transferred into ELISA plates and analyzed for ADCC as follows. ADCC is monitored by lactate dehydrogenase (LDH) release, an endogenous enzyme used to measure ADCC in standard assays. LDH is monitored by adding 100 ul of LDH substrate (Roche), a chemical that when converted by LDH is spectrophotometrically detectable at $OD_{490}$, to supernatant and incubated for 10 minutes at ambient temperature. LDH activity is proportional to the extent of the LDH enzyme released from lysed target cells. Optical density at 490 nm ($OD_{490}$) is obtained spectrophotometrically. 2% Triton X is added to effector cells alone as a "max" positive control, while target cells with PBMC and no antibody serve as the "spontaneous" negative control. LDH values are obtained and percent of cytotoxicity is determined with the formula: (sample value−spontaneous)/(max−spontaneous)× 100%, where 'spontaneous'=target cell lysis in absence of effector cells, and 'max'=target cell lysis in the presence of 2% Triton. Cytotoxicity elicited by 100 ng/ml of MORAb-A92 (protein A purified) will be used as positive control. Non-specific cytotoxicity will be monitored using 100 ng/ml of normal human IgG1 antibody. The ratio obtained by dividing the % cytotoxicity by the concentration of the antibody for each well/clone (i.e. ratio=50(%)/100(ng/ml)= 0.5) will be set as the criterion for selecting lead clones with potentially enhanced effector function.

Figure 2:
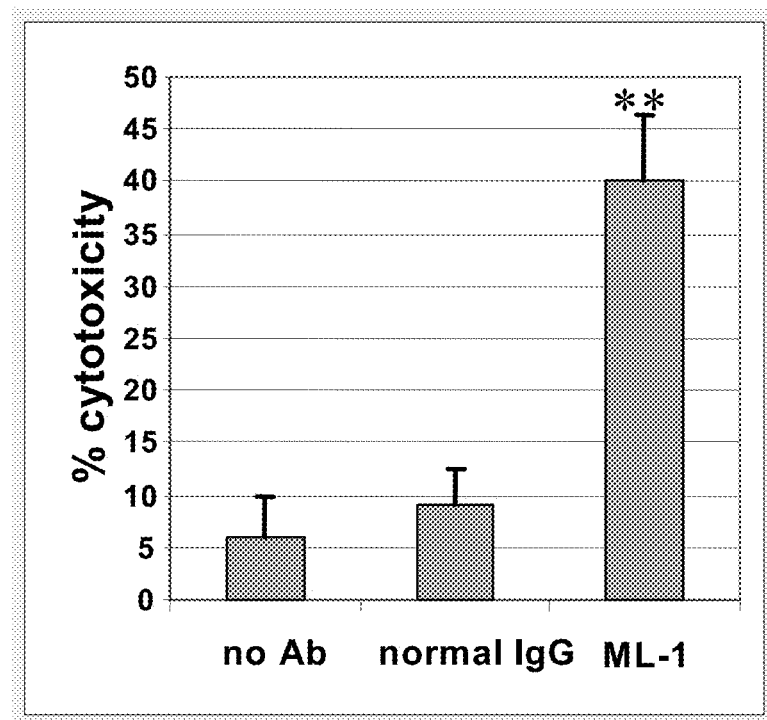
FIG. 2 demonstrates that ML-1 elicits a robust antibody-dependent cellular cytotoxicity (ADCC) activity. Tumor cell line OVCAR3 (referred to as target) which expresses FRA was incubated with human peripheral blood mononuclear cells (PBMCs) alone (no Ab lane); with ML-1; or control Ig (normal IgG). Cell cultures were assayed for killing by monitoring for lactate dehydrogenase (LDH) release that occurs upon cell lysis. ML-1 has ADCC activity on FRA-expressing cells.

Analysis of ML-1 shows the ability to enhance ADCC activity (p=0.018) over cells incubated with control Ig or no antibody (FIG. 2). FIG. 2 demonstrates that ML-1 elicits a robust antibody-dependent cellular cytotoxicity (ADCC) activity. Tumor cell line OVCAR3 (referred to as target) which expresses FRA was incubated with human PBMCs alone (no Ab lane); with ML-1; or control Ig (normal IgG). Cell cultures were assayed for killing by monitoring for lactate dehydrogenase (LDH) release that occurs upon cell lysis. ML-1 has ADCC activity on FRA-expressing cells. These data support the finding that ML-1 has cytotoxic effects via immune effector function.

Example 3

Figure 3:
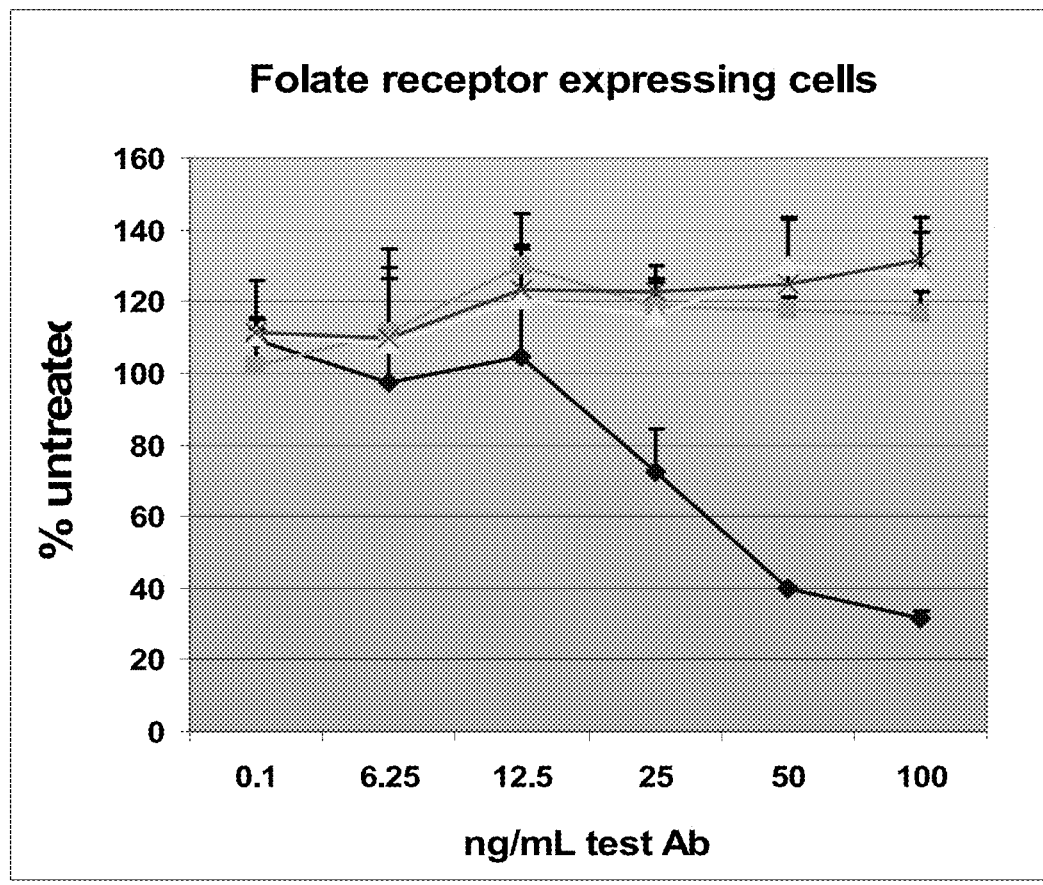
FIG. 3 demonstrates that ML-1 internalizes in FRA-expressing cells.

ML-1 internalizes when bound to FRA-expressing cells. This finding is shown in FIG. 3 using the Hum-ZAP assay. Second immunotoxins are conjugations of a secondary antibody to the ribosome inactivating protein saporin. If the primary antibody being tested is internalized, the saporin is transported into the cell via its binding to the secondary antibody. Once internalized saporin separates from its IgG conjugate, it inhibits protein synthesis and ultimately causes cell death. Hum-ZAP (Advanced Targeting Systems, cat# IT-22) is a secondary chemical conjugate of affinity purified goat anti-human IgG, (mw 210 kDa) that recognizes human monoclonal antibodies. The control molecule, Goat IgG-SAP (Advanced Targeting Systems cat#IT-19) is a conjugate of normal goat IgG and saporin. Briefly, cells are plated into flat-bottom 96-well tissue culture plates at 2500/well in 80 ul of RPMI 1640 with 10% FCS, 2.0 mM glutamine, 1.0 mM sodium pyruvate, and 0.1 mM MEM non-essential amino acids. Twenty-four hours later, 10 ul of primary antibodies ML-1 or MORAb-A92 are added along with 10 ul of Hum-ZAP or Goat IgG-SAP to bring the total volume to 100 ul. Experiments are set up with antibody titrations and include primary and secondary antibodies alone as control. Four days later, cell viability is evaluated using Promega CellTiter® Cytotoxicity Assay (cat# G3581) which reads viable cell number by spectrophotometry. All tests are performed in triplicate. Data is evaluated by comparing treated and untreated wells and results are expressed as percent of control. As shown in FIG. 3, ML-1 internalizes in OVCAR-3 cells which overexpress FRA. Cells die upon treatment with ML-1 linked to saporin (diamond) in contrast to ML-1 unconjugated (square), while an isotype control antibody MORAb-A92 did not kill cells in conjugated or unconjugated toxin form (triangle and X, respectively). As control, cells not expressing FRA were used and it was shown that ML-1 has no toxic effect in toxin-conjugated or unconjugated form. These data support the finding that ML-1 internalizes in FRA-bearing cells.

What is claimed:

1. A method for treating folate receptor-alpha-positive ovarian cancer in a subject in need of treatment of the cancer, the method comprising administering to the subject a therapeutically effective amount of doxorubicin and a therapeutically effective amount of the antibody produced by cells assigned American Type Culture Collection accession number PTA-7552, wherein the antibody is conjugated to a carbohydrate and/or chemotherapeutic agent.

2. The method of claim 1 wherein the antibody is humanized.

3. The method of claim 1 wherein the subject is human.

4. The method of claim 1 wherein the administering of the antibody comprises injecting or infusing the antibody.

5. The method of claim 1 wherein the antibody is conjugated to a carbohydrate.

6. The method of claim 1 wherein the antibody is conjugated to a chemotherapeutic agent.

7. A method for treating folate receptor-alpha-positive ovarian cancer in a subject in need of treatment of the cancer, the method comprising administering to the subject a therapeutically effective amount of paclitaxel and a therapeutically effective amount of the antibody produced by cells assigned American Type Culture Collection accession number PTA-7552, wherein the antibody is conjugated to a carbohydrate and/or chemotherapeutic agent.

8. The method of claim 7 wherein the antibody is humanized.

9. The method of claim 7 wherein the subject is human.

10. The method of claim 7 wherein the administering of the antibody comprises injecting or infusing the antibody.

11. The method of claim 7 wherein the antibody is conjugated to a carbohydrate.

12. The method of claim 7 wherein the antibody is conjugated to a chemotherapeutic agent.

* * * * *

SEQUENCE LISTING

```
<160> NUMBER OF SEQ ID NOS: 2

<210> SEQ ID NO 1
<211> LENGTH: 696
<212> TYPE: DNA
<213> ORGANISM: Homo sapiens
```

<400> SEQUENCE: 1

```
attgcatggg ccaggactga gcttctcaat gtctgcatga acgccaagca ccacaaggaa      60
aagccaggcc ccgaggacaa gttgcatgag cagtgtcgac cctggaggaa gaatgcctgc     120
tgttctacca acaccagcca ggaagcccat aaggatgttt cctacctata tagattcaac     180
tggaaccact gtggagagat ggcacctgcc tgcaaacggc atttcatcca ggacacctgc     240
ctctacgagt gctcccccaa cttggggccc tggatccagc aggtggatca gagctggcgc     300
aaagagcggg tactgaacgt gcccctgtgc aaagaggact gtgagcaatg gtgggaagat     360
tgtcgcacct cctacacctg caagagcaac tggcacaagg gctggaactg gacttcaggg     420
tttaacaagt gcgcagtggg agctgcctgc caaccttttcc atttctactt ccccacaccc     480
actgttctgt gcaatgaaat ctggactcac tcctacaagg tcagcaacta cagccgaggg     540
agtggccgct gcatccagat gtggttcgac ccagcccagg gcaaccccaa tgaggaggtg     600
gcgaggttct atgctgcagc catgagtggg gctgggccct gggcagcctg gcctttcctg     660
cttagcctgg ccctaatgct gctgtggctg ctcagc                                696
```

<210> SEQ ID NO 2
<211> LENGTH: 232
<212> TYPE: PRT
<213> ORGANISM: Homo sapiens

<400> SEQUENCE: 2

```
Ile Ala Trp Ala Arg Thr Glu Leu Leu Asn Val Cys Met Asn Ala Lys
1               5                   10                  15

His His Lys Glu Lys Pro Gly Pro Glu Asp Lys Leu His Glu Gln Cys
            20                  25                  30

Arg Pro Trp Arg Lys Asn Ala Cys Cys Ser Thr Asn Thr Ser Gln Glu
        35                  40                  45

Ala His Lys Asp Val Ser Tyr Leu Tyr Arg Phe Asn Trp Asn His Cys
    50                  55                  60

Gly Glu Met Ala Pro Ala Cys Lys Arg His Phe Ile Gln Asp Thr Cys
65                  70                  75                  80

Leu Tyr Glu Cys Ser Pro Asn Leu Gly Pro Trp Ile Gln Gln Val Asp
                85                  90                  95

Gln Ser Trp Arg Lys Glu Arg Val Leu Asn Val Pro Leu Cys Lys Glu
            100                 105                 110

Asp Cys Glu Gln Trp Trp Glu Asp Cys Arg Thr Ser Tyr Thr Cys Lys
        115                 120                 125

Ser Asn Trp His Lys Gly Trp Asn Trp Thr Ser Gly Phe Asn Lys Cys
    130                 135                 140

Ala Val Gly Ala Ala Cys Gln Pro Phe His Phe Tyr Phe Pro Thr Pro
145                 150                 155                 160

Thr Val Leu Cys Asn Glu Ile Trp Thr His Ser Tyr Lys Val Ser Asn
                165                 170                 175

Tyr Ser Arg Gly Ser Gly Arg Cys Ile Gln Met Trp Phe Asp Pro Ala
            180                 185                 190

Gln Gly Asn Pro Asn Glu Glu Val Ala Arg Phe Tyr Ala Ala Ala Met
        195                 200                 205

Ser Gly Ala Gly Pro Trp Ala Ala Trp Pro Phe Leu Leu Ser Leu Ala
    210                 215                 220

Leu Met Leu Leu Trp Leu Leu Ser
225                 230
```